United States Patent
Watanabe et al.

(10) Patent No.: US 9,068,055 B2
(45) Date of Patent: Jun. 30, 2015

(54) RUBBER COMPOSITION

(75) Inventors: Yosuke Watanabe, Osaka (JP); Orhan Ozturk, Osaka (JP); Yasuo Uekita, Osaka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

(21) Appl. No.: 14/110,043

(22) PCT Filed: Apr. 24, 2012

(86) PCT No.: PCT/JP2012/061513
§ 371 (c)(1),
(2), (4) Date: Oct. 4, 2013

(87) PCT Pub. No.: WO2012/147984
PCT Pub. Date: Nov. 1, 2012

(65) Prior Publication Data
US 2014/0020808 A1    Jan. 23, 2014

(30) Foreign Application Priority Data

Apr. 26, 2011 (JP) ................................ 2011-097981
Mar. 1, 2012 (JP) ................................ 2012-045077

(51) Int. Cl.
C08K 5/20     (2006.01)
B60C 1/00     (2006.01)
C08K 5/17     (2006.01)
C08L 21/00    (2006.01)

(52) U.S. Cl.
CPC ............. *C08K 5/20* (2013.01); *Y10T 152/1081* (2015.01); *Y10T 152/10495* (2015.01); *B60C 1/00* (2013.01); *C08K 5/17* (2013.01); *B60C 1/0008* (2013.04); *B60C 1/0016* (2013.04); *B60C 1/0025* (2013.04); *B60C 1/0041* (2013.04)

(58) Field of Classification Search
CPC .............. C08K 5/20; C08K 5/17; B60C 1/00; C08L 21/00; Y10T 152/1081; Y10T 152/10495
USPC .......... 524/236, 217; 152/525, 537, 564, 450; 562/433; 560/43
See application file for complete search history.

(56) References Cited

U.S. PATENT DOCUMENTS

| | | | |
|---|---|---|---|
| 4,376,189 A * | 3/1983 | Trivette ........................ | 525/291 |
| 4,433,114 A | 2/1984 | Coran et al. | |
| 5,106,913 A | 4/1992 | Yamaguchi et al. | |
| 5,175,309 A | 12/1992 | Tsumura et al. | |
| 5,872,167 A | 2/1999 | Wideman et al. | |
| 7,442,733 B2 * | 10/2008 | Araujo Da Silva et al. .. | 524/105 |
| 2001/0027235 A1 * | 10/2001 | Onizawa ........................ | 525/133 |
| 2006/0247342 A1 | 11/2006 | Da Silva et al. | |

FOREIGN PATENT DOCUMENTS

| | | |
|---|---|---|
| EP | 0080451 A1 | 6/1983 |
| EP | 0476310 A2 | 3/1990 |
| EP | 2009049 A1 | 12/2008 |
| JP | 58-89632 A | 5/1983 |
| JP | 58-89633 A | 5/1983 |
| JP | 06-116236 A | 4/1994 |
| JP | 2001-226489 A | 8/2001 |
| JP | 2006-225598 A | 8/2006 |
| JP | 2007-505957 A | 3/2007 |

OTHER PUBLICATIONS

"Dynamic test (JIS K 63944)," Rubber Technology Introduction, pp. 122-125, published by Maruzen Co., Ltd., edited by the Society of Rubber Science and Technology, Japan.

Shang-Ju Hsieh et al., "Synthesis and Structural Characterization of Dendritic-Linear PMA-APM-r-PS. Copolymers for a Self-Assembled Microporous Matrix," Journal of Polymer Science: Part A: Polymer Chemistry, 2010, pp. 3290-3301, vol. 48, published by Wiley Periodicals, Inc.

Malcom Siegel et al., "The Reactions of Antiserum Homologous to the p-Azomaleanilate and p-Azofumaranilate Ion Groups," Journal of the American Chemical Society, Jun. 5, 1954, pp. 2863-2866, vol. 76.

C. L. Sharma et al., "Maleanilic Acids as Highly Selective Reagents for the Amperometric Determination of Thorium (IV)," Analytical Letters, 1979, pp. 1005-1008, vol. 12(A9), published by Marcel Dekker, Inc.

International Preliminary Report on Patentability and Written Opinion mailed Nov. 7, 2013 in International Application No. PCT/JP2012/061513.

Extended European Search Report issued Dec. 4, 2014 in corresponding European Patent Application No. 12777208.5.

* cited by examiner

*Primary Examiner* — Michael M Bernshteyn
(74) *Attorney, Agent, or Firm* — Sughrue Mion, PLLC

(57) ABSTRACT

A rubber composition obtained by kneading at least one selected from the group consisting of (A1), (B1), (C1) and (D1), a rubber component and a filler, and a method of improving the viscoelastic property of vulcanized rubber, comprising a first step of kneading at least one selected from the group consisting of (A1), (B1), (C1) and (D1), a rubber component, a filler and a sulfur component and a second step of thermally treating the kneaded material obtained in the previous step.

(A1): a compound represented by formula (I)
(B1): a salt of a compound represented by formula (I)
(C1): a solvate of a compound represented by formula (I)
(D1): a solvate of a salt of a compound represented by formula (I).

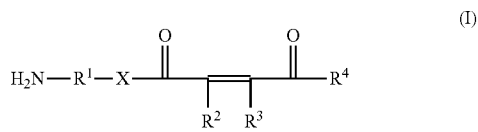

(I)

2 Claims, No Drawings

RUBBER COMPOSITION

CROSS REFERENCE TO RELATED APPLICATIONS

This is a National Stage of International Application No. PCT/JP2012/061513 filed Apr. 24, 2012, claiming priority based on Japanese Patent Application No. 2011-097981 filed Apr. 26, 2011, and Japanese Application No. 2012-045077 filed and Mar. 1, 2012, the contents of all of which are incorporated herein by reference in their entirety.

TECHNICAL FIELD

The present invention relates to a rubber composition and the like.

BACKGROUND ART

Recently, an improvement in the fuel consumption of automobiles (namely, lowering of fuel consumption) has been desired by the request of the environmental protection. In the field of automobile tires, it is known that the fuel consumption of automobiles goes down by improving the viscoelastic property of vulcanized rubber used for tire production (see, "Rubber Technology Introduction", p. 124 edited by The Society of Rubber Science and Technology, Japan, published by Maruzen Co., Ltd.).

DISCLOSURE OF THE INVENTION

The present invention includes the following parts.

[1] A rubber composition obtained by kneading at least one selected from the group consisting of (A1), (B1), (C1) and (D1), a rubber component and a filler:
(A1): a compound represented by formula (I)
(B1): a salt of a compound represented by formula (I)
(C1): a solvate of a compound represented by formula (I)
(D1): a solvate of a salt of a compound represented by formula (I):

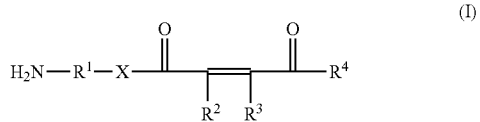
(I)

in formula (I), $R^1$ represents an optionally substituted alkanediyl group having 2 to 12 carbon atoms, an optionally substituted cycloalkanediyl group having 3 to 12 carbon atoms or a *—$B^1$—Ar—$B^2$—* group, * represents a connecting bond, $B^1$ represents a single bond or an alkanediyl group having 1 to 12 carbon atoms, $B^2$ represents a single bond or an alkanediyl group having 1 to 12 carbon atoms, Ar represents an optionally substituted di-valent aromatic hydrocarbon group having 6 to 12 carbon atoms, $R^2$ and $R^3$ represent each independently a hydrogen atom, a halogen atom, an alkyl group having 1 to 6 carbon atoms, an aryl group having 6 to 12 carbon atoms, a hydroxy group or an alkoxy group having 1 to 6 carbon atoms, alternatively, are mutually linked to form an alkanediyl group having 2 to 12 carbon atoms, $R^4$ represents a hydroxy group, an alkoxy group having 1 to 6 carbon atoms, an aryloxy group having 6 to 12 carbon atoms, an aryl alkoxy group having 7 to 15 carbon atoms or —$NR^5R^6$, $R^5$ and $R^6$ represent each independently a hydrogen atom or an alkyl group having 1 to 6 carbon atoms, and X represents —NH— or —O—.

[2] The rubber composition according to [1], obtained by kneading at least one selected from the group consisting of (A2), (B2), (C2) and (D2), a rubber component and a filler:
(A2): a compound represented by formula (I-1)
(B2): a salt represented by formula (I-1)
(C2): a solvate of a compound represented by formula (I-1)
(D2): a solvate of a salt represented by formula (I-1):

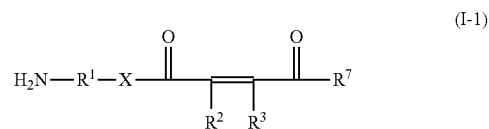
(I-1)

in formula (I-1), $R^1$ represents an optionally substituted alkanediyl group having 2 to 12 carbon atoms, an optionally substituted cycloalkanediyl group having 3 to 12 carbon atoms or a *—$B^1$—Ar—$B^2$—* group, * represents a connecting bond, $B^1$ represents a single bond or an alkanediyl group having 1 to 12 carbon atoms, $B^2$ represents a single bond or an alkanediyl group having 1 to 12 carbon atoms, Ar represents an optionally substituted di-valent aromatic hydrocarbon group having 6 to 12 carbon atoms, $R^2$ and $R^3$ represent each independently a hydrogen atom, a halogen atom, an alkyl group having 1 to 6 carbon atoms, an aryl group having 6 to 12 carbon atoms, a hydroxy group or an alkoxy group having 1 to 6 carbon atoms, alternatively, are mutually linked to form an alkanediyl group having 2 to 12 carbon atoms, $R^7$ represents a hydroxy group, an alkoxy group having 1 to 6 carbon atoms, an aryloxy group having 6 to 12 carbon atoms, an arylalkoxy group having 7 to 15 carbon atoms, —$NR^5R^6$ or —$O^-(Y^{n+})^{1/n}$, $R^5$ and $R^6$ represent each independently a hydrogen atom or an alkyl group having 1 to 6 carbon atoms, $Y^{n+}$ represents an n-valent cation, n represents 1 or 2, and X represents —NH— or —O—.

[3] The rubber composition according to [1] or [2], wherein $R^2$ and $R^3$ represent a hydrogen atom.

[4] The rubber composition according to any one of [1] to [3], wherein the compound represented by formula (I) is a compound represented by formula (II):

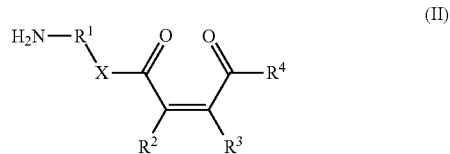
(II)

in formula (II), $R^1$, $R^2$, $R^3$, $R^4$ and X are each as described above.

[5] The rubber composition according to any one of [1] to [4], wherein $R^1$ represents an optionally substituted di-valent aromatic hydrocarbon group having 6 to 12 carbon atoms, and X represents —NH—.

[6] The rubber composition according to any one of [2] to [5], wherein $R^7$ represents a hydroxy group or —$O^-(Y^{n+})^{1/n}$.

[7] The rubber composition according to any one of [1] to [6], wherein the rubber component is natural rubber.

[8] The rubber composition according to any one of [1] to [7], obtained by kneading at least one selected from the group consisting of (A1), (B1), (C1) and (D1), a rubber component, a filler and a sulfur component.

[9] A vulcanized rubber obtained by thermally treating the rubber composition according to [8].

[10] A pneumatic tire produced by processing the rubber composition according to [8].

[11] A belt for tire containing a steel cord coated by the vulcanized rubber according to [9].

[12] A carcass for tire containing a carcass fiber cord coated by the vulcanized rubber according to [9].

[13] A side wall for tire, an inner liner for tire, a cap tread for tire or an under tread for tire containing the vulcanized rubber according to [9].

[14] A pneumatic tire containing the vulcanized rubber according to [9].

[15] A method of improving the viscoelastic property of a vulcanized rubber, comprising a first step of kneading at least one selected from the group consisting of (A1), (B1), (C1) and (D1), a rubber component, a filler and a sulfur component and a second step of thermally treating the kneaded material obtained in the previous step:
(A1): a compound represented by formula (I)
(B1): a salt of a compound represented by formula (I)
(C1): a solvate of a compound represented by formula (I)
(D1): a solvate of a salt of a compound represented by formula (I):

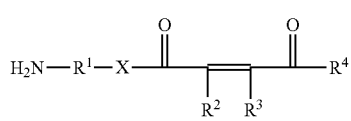

in formula (I), $R^1$ represents an optionally substituted alkanediyl group having 2 to 12 carbon atoms, an optionally substituted cycloalkanediyl group having 3 to 12 carbon atoms, an optionally substituted arylene group having 6 to 12 carbon atoms, an aralkylene group having 7 to 15 carbon atoms or an alkarylene group having 8 to 18 carbon atoms, $R^2$ and $R^3$ represent each independently a hydrogen atom, a halogen atom, an alkyl group having 1 to 6 carbon atoms, an aryl group having 6 to 12 carbon atoms, a hydroxy group or an alkoxy group having 1 to 6 carbon atoms, alternatively, are mutually linked to form an alkanediyl group having 2 to 12 carbon atoms, $R^4$ represents a hydroxy group, an alkoxy group having 1 to 6 carbon atoms, an aryloxy group having 6 to 12 carbon atoms, an arylalkoxy group having 7 to 15 carbon atoms or —$NR^5R^6$, $R^5$ and $R^6$ represent each independently a hydrogen atom or an alkyl group having 1 to 6 carbon atoms, and X represents —NH— or —O—.

[16] Use of at least one selected from the group consisting of (A1), (B1), (C1) and (D1), for improving the viscoelastic property of a vulcanized rubber:
(A1): a compound represented by formula (I)
(B1): a salt of a compound represented by formula (I)
(C1): a solvate of a compound represented by formula (I)
(D1): a solvate of a salt of a compound represented by formula (I):

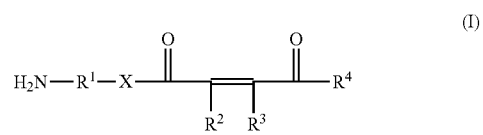

in formula (I), $R^1$ represents an optionally substituted alkanediyl group having 2 to 12 carbon atoms, an optionally substituted cycloalkanediyl group having 3 to 12 carbon atoms or a *—$B^1$—Ar—$B^2$—* group, * represents a connecting bond, $B^1$ represents a single bond or an alkanediyl group having 1 to 12 carbon atoms, $B^2$ represents a single bond or an alkanediyl group having 1 to 12 carbon atoms, Ar represents an optionally substituted di-valent aromatic hydrocarbon group having 6 to 12 carbon atoms, $R^2$ and $R^3$ represent each independently a hydrogen atom, a halogen atom, an alkyl group having 1 to 6 carbon atoms, an aryl group having 6 to 12 carbon atoms, a hydroxy group or an alkoxy group having 1 to 6 carbon atoms, alternatively, are mutually linked to form an alkanediyl group having 2 to 12 carbon atoms, $R^4$ represents a hydroxy group, an alkoxy group having 1 to 6 carbon atoms, an aryloxy group having 6 to 12 carbon atoms, an arylalkoxy group having 7 to 15 carbon atoms or —$NR^5R^6$, $R^5$ and $R^6$ represent each independently a hydrogen atom or an alkyl group having 1 to 6 carbon atoms, and X represents —NH— or —O—.

[17] A vulcanized rubber viscoelastic property improving agent, comprising at least one selected from the group consisting of (A1), (B1), (C1) and (D1) as an active ingredient:
(A1): a compound represented by formula (I)
(B1): a salt of a compound represented by formula (I)
(C1): a solvate of a compound represented by formula (I)
(D1): a solvate of a salt of a compound represented by formula (I):

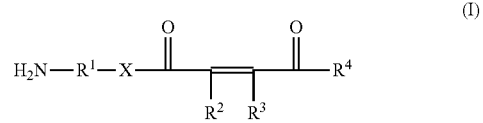

in formula (I), $R^1$ represents an optionally substituted alkanediyl group having 2 to 12 carbon atoms, an optionally substituted cycloalkanediyl group having 3 to 12 carbon atoms or a *—$B^1$—Ar—$B^2$—* group, * represents a connecting bond, $B^1$ represents a single bond or an alkanediyl group having 1 to 12 carbon atoms, $B^2$ represents a single bond or an alkanediyl group having 1 to 12 carbon atoms, Ar represents an optionally substituted di-valent aromatic hydrocarbon group having 6 to 12 carbon atoms, $R^2$ and $R^3$ represent each independently a hydrogen atom, a halogen atom, an alkyl group having 1 to 6 carbon atoms, an aryl group having 6 to 12 carbon atoms, a hydroxy group or an alkoxy group having 1 to 6 carbon atoms, alternatively, are mutually linked to form an alkanediyl group having 2 to 12 carbon atoms, $R^4$ represents a hydroxy group, an alkoxy group having 1 to 6 carbon atoms, an aryloxy group having 6 to 12 carbon atoms, an arylalkoxy group having 7 to 15 carbon atoms or —NR$^5$R$^6$, R$^5$ and R$^6$ represent each independently a hydrogen atom or an alkyl group having 1 to 6 carbon atoms, and X represents —NH— or —O—.

[18] A salt represented by formula (III):

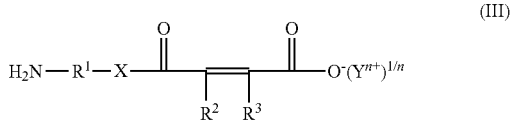

(III)

in formula (III),

R$^1$ represents an optionally substituted alkanediyl group having 2 to 12 carbon atoms, an optionally substituted cycloalkanediyl group having 3 to 12 carbon atoms or a *—B$^1$—Ar—B$^2$—* group, * represents a connecting bond, B1 represents a single bond or an alkanediyl group having 1 to 12 carbon atoms, B$^2$ represents a single bond or an alkanediyl group having 1 to 12 carbon atoms, Ar represents an optionally substituted di-valent aromatic hydrocarbon group having 6 to 12 carbon atoms, R$^2$ and R$^3$ represent each independently a hydrogen atom, a halogen atom, an alkyl group having 1 to 6 carbon atoms, an aryl group having 6 to 12 carbon atoms, a hydroxy group or an alkoxy group having 1 to 6 carbon atoms, alternatively, are mutually linked to form an alkanediyl group having 2 to 12 carbon atoms, Y$^{n+}$ represents an n-valent metal cation, NH$_4^+$ or an n-valent organic cation, n represents 1 or 2, and X represents —NH— or —O—.

[19] A hydrate of the salt represented by formula (III) according to [18].

[20] A hydrate of a compound represented by formula (I-2) or a salt thereof:

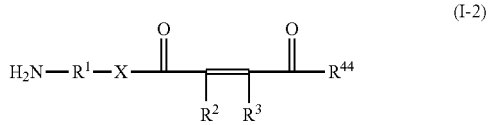

(I-2)

in formula (I-2),

R$^1$ represents an optionally substituted alkanediyl group having 2 to 12 carbon atoms, an optionally substituted cycloalkanediyl group having 3 to 12 carbon atoms or a *—B$^1$—Ar—B$^2$—* group, * represents a connecting bond, B1 represents a single bond or an alkanediyl group having 1 to 12 carbon atoms, B$^2$ represents a single bond or an alkanediyl group having 1 to 12 carbon atoms, Ar represents an optionally substituted di-valent aromatic hydrocarbon group having 6 to 12 carbon atoms, R$^2$ and R$^3$ represent each independently a hydrogen atom, a halogen atom, an alkyl group having 1 to 6 carbon atoms, an aryl group having 6 to 12 carbon atoms, a hydroxy group or an alkoxy group having 1 to 6 carbon atoms, alternatively, are mutually linked to form an alkanediyl group having 2 to 12 carbon atoms, R$^{44}$ represents an alkoxy group having 1 to 6 carbon atoms, an aryloxy group having 6 to 12 carbon atoms, an arylalkoxy group having 7 to 15 carbon atoms or —NR$^5$R$^6$, R$^5$ and R$^6$ represent each independently a hydrogen atom or an alkyl group having 1 to 6 carbon atoms, and X represents —NH— or —O—.

[21] A methanol solvate of a compound represented by formula (I) or a salt thereof:

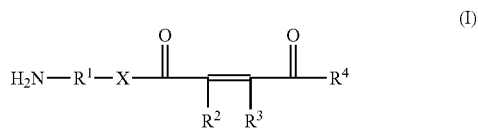

(I)

in formula (I),

R$^1$ represents an optionally substituted alkanediyl group having 2 to 12 carbon atoms, an optionally substituted cycloalkanediyl group having 3 to 12 carbon atoms or a *—B$^1$—Ar—B$^2$—* group, * represents a connecting bond, B$^1$ represents a single bond or an alkanediyl group having 1 to 12 carbon atoms, B$^2$ represents a single bond or an alkanediyl group having 1 to 12 carbon atoms, Ar represents an optionally substituted di-valent aromatic hydrocarbon group having 6 to 12 carbon atoms, R$^2$ and R$^3$ represent each independently a hydrogen atom, a halogen atom, an alkyl group having 1 to 6 carbon atoms, an aryl group having 6 to 12 carbon atoms, a hydroxy group or an alkoxy group having 1 to 6 carbon atoms, alternatively, are mutually linked to form an alkanediyl group having 2 to 12 carbon atoms, R$^4$ represents a hydroxy group, an alkoxy group having 1 to 6 carbon atoms, an aryloxy group having 6 to 12 carbon atoms, an arylalkoxy group having 7 to 15 carbon atoms or —NR$^5$R$^6$, R$^5$ and R$^6$ represent each independently a hydrogen atom or an alkyl group having 1 to 6 carbon atoms, and X represents —NH— or —O—.

MODES FOR CARRYING OUT THE INVENTION

The present invention will be explained in detail below.

In the present invention, "improving the viscoelastic property" includes, for example, a modification of the loss coefficient (tan δ) of vulcanized rubber as described below.

The present invention is a rubber composition obtained by kneading at least one selected from the group consisting of (A1), (B1), (C1) and (D1), a rubber component and a filler:

(A1): a compound represented by formula (I) (hereinafter, referred to as "compound (I)")

(B1): a salt of a compound (I)

(C1): a solvate of a compound (I)

(D1): a solvate of a salt of a compound (I).

<Compound (I)>

The salt of a compound (I) includes a carboxylate salt of a compound (I) in which R$^4$ is a hydroxy group, and an addition salt formed at an amine portion (—NH$_2$ or —NH—) in a compound (I) together with an acid.

The carboxylate salt of a compound (I) includes, for example, salts in which R$^7$ is —O$^-$(Y$^{n+}$)$^{1/n}$ in a compound represented by formula (I-1) or a salt thereof.

The acid in the addition salt formed at an amine portion in a compound (I) together with the acid includes inorganic acids and organic acids.

The solvate includes a methanol solvate, a hydrate and the like.

The compound having a linkage between a carbon-carbon double bond and R$^3$ and CO—R$^4$ in a compound (I) may be any of a compound containing an E-configured carbon-carbon double bond, a compound containing a Z-configured carbon-carbon double bond, or a mixture of an E-configured compound and a Z-configured compound. Particularly, a compound containing a Z-configured carbon-carbon double bond is preferable.

As the compound (I), a compound represented by formula (II) is preferable.

The alkanediyl group having 2 to 12 carbon atoms in $R^1$ includes, for example, linear alkanediyl groups such as a methylene group, an ethylene group, a trimethylene group, a tetramethylene group, a pentamethylene group and a hexamethylene group; and branched alkanediyl groups such as an isopropylene group, an isobutylene group, a 2-methyltrimethylene group, an isopentylene group, an isohexylene group, an isooctylene group, a 2-ethylhexylene group and an isodecylene group. Particularly, the number of carbon atoms of the alkanediyl group is preferably 3 to 12, more preferably 3 to 6. Linear alkanediyl groups are preferable.

The substituent optionally carried on the alkanediyl group includes, for example, alkoxy groups having 1 to 4 carbon atoms such as a methoxy group, an ethoxy group and a butoxy group, halogen atoms such as chlorine, bromine, iodine and fluorine, aryl groups having 6 to 12 carbon atoms such as a phenyl group, a naphthyl group and a biphenyl group, and a hydroxy group. The alkanediyl group carrying a substituent includes, for example, the following groups. * represents a connecting bond.

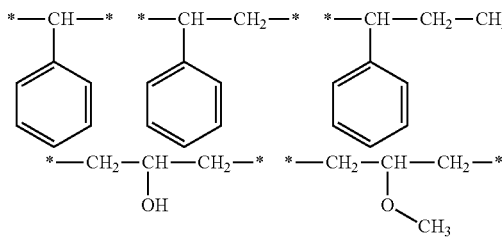

The cycloalkanediyl group having 3 to 12 carbon atoms in $R^1$ includes, for example, a cyclopropylene group, a cyclopentylene group, a cyclohexylene group and a cyclododecylene group.

The substituent optionally carried on the cycloalkanediyl group having 3 to 12 carbon atoms includes, for example, alkyl groups having 1 to 4 carbon atoms such as a methyl group, an ethyl group, a n-propyl group, a n-butyl group and a t-butyl group; aryl groups having 6 to 10 carbon atoms such as a phenyl group, a 4-methylphenyl group and a naphthyl group; alkoxy groups having 1 to 4 carbon atoms such as a methoxy group, an ethoxy group and a n-butoxy group; acyl groups having 1 to 7 carbon atoms such as an acetyl group, a benzoyl group, a formyl group and a pivaloyl group; alkoxycarbonyl groups having 3 to 4 carbon atoms such as a methoxycarbonyl group and an ethoxycarbonyl group; aryloxycarbonyl groups having 7 to 11 carbon atoms such as a phenoxycarbonyl group and a naphthyloxycarbonyl group; acyloxy groups having 2 to 7 carbon atoms such as an acetoxy group and a benzoyloxy group; etc.

Preferable as the cycloalkanediyl group having 3 to 12 carbon atoms are a cyclopentylene group, a cyclohexylene group, a methylcyclohexylene group and a t-butylcyclohexylene group.

The alkanediyl group having 1 to 12 carbon atoms in $B^1$ and $B^2$ includes the same groups as described above and a methylene group.

The di-valent aromatic hydrocarbon group having 6 to 12 carbon atoms in Ar includes a phenylene group, a naphthylene group, a biphenylene group and the like.

The *—$B^1$—Ar—$B^2$—* group in $R^1$ includes, for example, a phenylene group, a naphthylene group, a biphenylene group and the following groups. * represents a connecting bond.

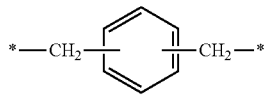

A hydrogen atom contained in Ar may be substituted by at least one group selected from the group consisting of alkyl groups having 1 to 4 carbon atoms, alkoxy groups having 1 to 4 carbon atoms, a hydroxy group, a nitro group, a cyano group, a sulfo group and halogen atoms.

As $R^1$, preferable are alkylene groups having 2 to 12 carbon atoms, a phenylene group or the following groups, more preferable is a phenylene group.

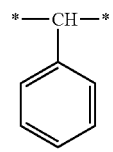 [SMILES: *C(*)c1ccccc1]

The halogen atom in $R^2$ and $R^3$ includes fluorine, chlorine, bromine and iodine.

The alkyl group having 1 to 6 carbon atoms in $R^2$ and $R^3$ includes, for example, a methyl group, an ethyl group, a n-propyl group, an isopropyl group, a n-butyl group, an isobutyl group, a sec-butyl group, a tert-butyl group, a n-pentyl group, an isopentyl group and a n-hexyl group.

The aryl group having 6 to 12 carbon atoms in $R^2$ and $R^3$ denotes a mono-cyclic or condensed poly-cyclic aromatic hydrocarbon having 6 to 12 carbon atoms, and examples thereof includes a phenyl group, a naphthyl group and a biphenyl group.

The alkoxy group having 1 to 6 carbon atoms in $R^2$ and $R^3$ includes, for example, a methoxy group, an ethoxy group, a n-propoxy group, an isopropoxy group, a n-butoxy group, an isobutoxy group, a sec-butoxy group, a tert-butoxy group, a n-pentoxy group, an isopentoxy group and a n-hexyloxy group.

The alkanediyl group having 2 to 12 carbon atoms formed by mutually linking $R^2$ and $R^3$ includes the same groups as described above, and alkanediyl groups having 3 or 4 carbon atoms are preferable. The cyclic structure formed by $R^2$ and $R^3$ together with carbon atoms to which they are linked includes, for example, a cyclopentene ring and a cyclohexene ring.

It is preferable that $R^2$ is a hydrogen atom and $R^3$ is a hydrogen atom or an alkyl group having 1 to 6 carbon atoms, it is more preferable that $R^2$ and $R^3$ represent a hydrogen atom.

The alkoxy group having 1 to 6 carbon atoms in $R^4$, $R^4$ and $R^7$ includes the same groups as described above.

The aryloxy group having 6 to 12 carbon atoms in $R^4$, $R^4$ and $R^7$ includes groups obtained by linking an oxy group to the above-described aryl group having 6 to 12 carbon atoms, and examples thereof include a phenyloxy group, a naphthyloxy group and a biphenyloxy group.

The arylalkoxy group having 7 to 15 carbon atoms in $R^4$, $R^4$ and $R^7$ includes a phenylethyloxy group, a benzyloxy group, a phenylpropyloxy and the like.

—$NR^5R^6$ in $R^4$, $R^4$ and $R^7$ includes a methylamino group, an ethylamino group, a phenylamino group, an ethylmethylamino group, a dimethylamino group, a diethylamino group, a methylphenylamino group, an ethylphenylamino group, a diphenylamino group and the like.

$Y^{n+}$ in $R^7$ represents an n-valent cation capable of forming a carboxylate salt represented by formula (I).

$Y^+$ includes cations of metals selected from the group consisting of alkali metals, alkaline earth metals and transition elements of groups IB and IIB of the periodic table, cations of organic bases capable of forming a salt with a carboxy group such as amines, etc., and examples thereof include $Li^+$, $Na^+$, $K^+$, $Mg^{2+}$, $Ca^{2+}$, $Ba^{2+}$, $Zn^{2+}$, $Cu^{2+}$, $Cu^+$, $Ag^+$, $(NH_4)^+$, $[NH(C_2H_5)_3]^+$, $[NH(C_2H_5)(i\text{-}C_3H_7)_2]$, $H_3N\text{—}(CH_2)_2\text{—}NH_3^+$ and $^+H_3N\text{—}(CH_2)\text{—}NH_3^+$.

As $R^4$, a hydroxy group is preferable. As $R^7$, a hydroxy group or —$O^-(Y^{n+})^{1/n}$ is preferable, a hydroxy group or —$O^-(Y^{n+})^{1/n}$ (Y is an alkali metal) is more preferable.

Specific examples of the compound (I) are shown below.

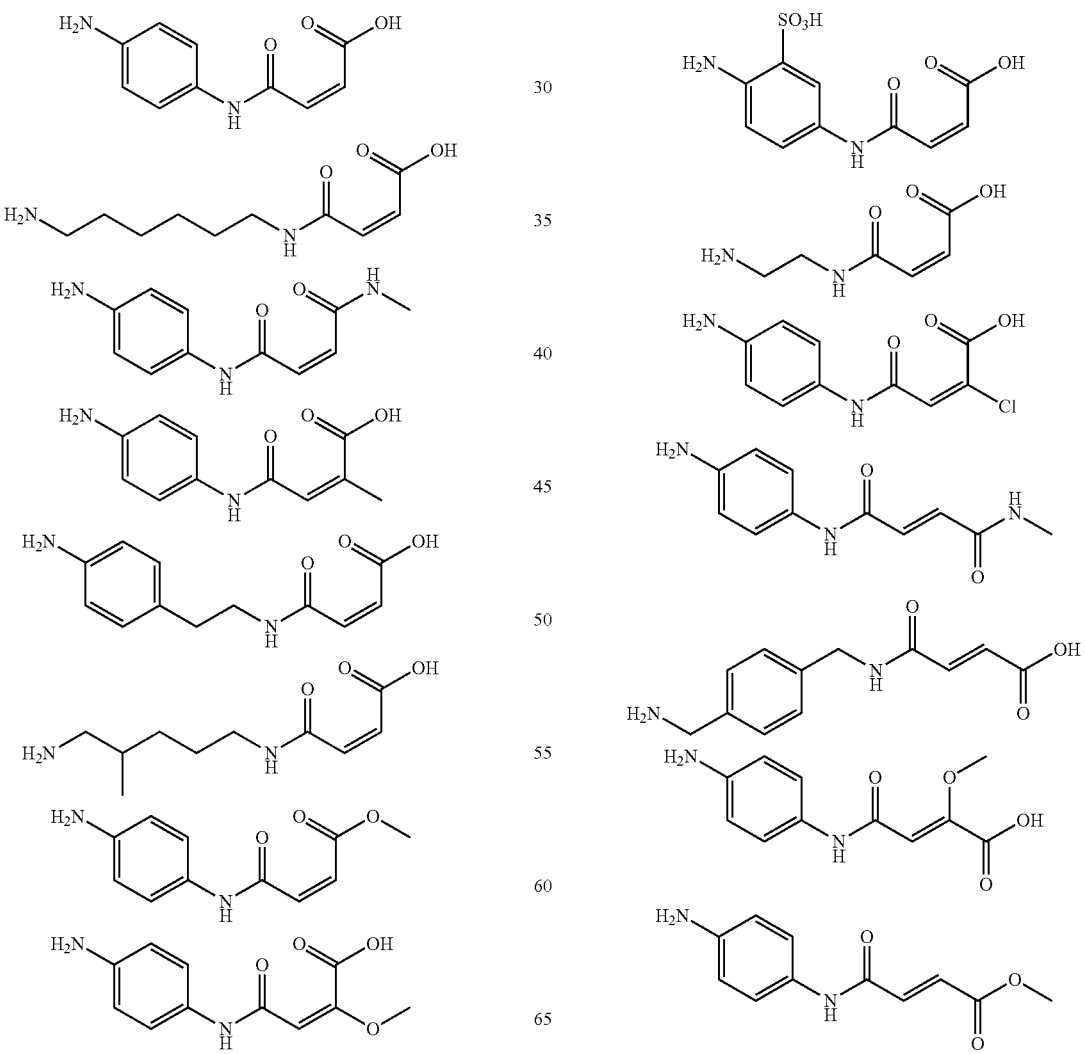

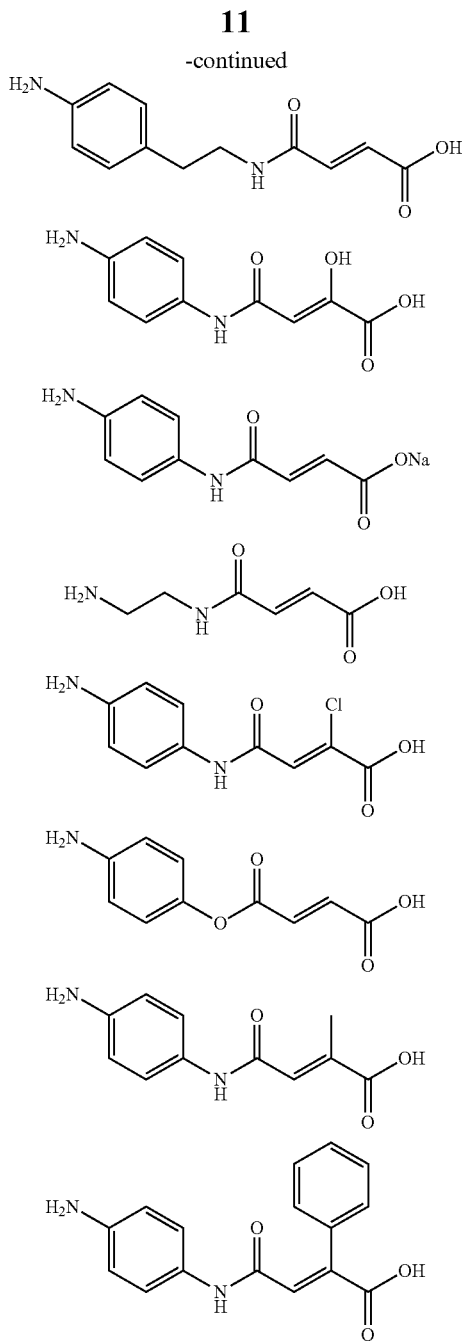

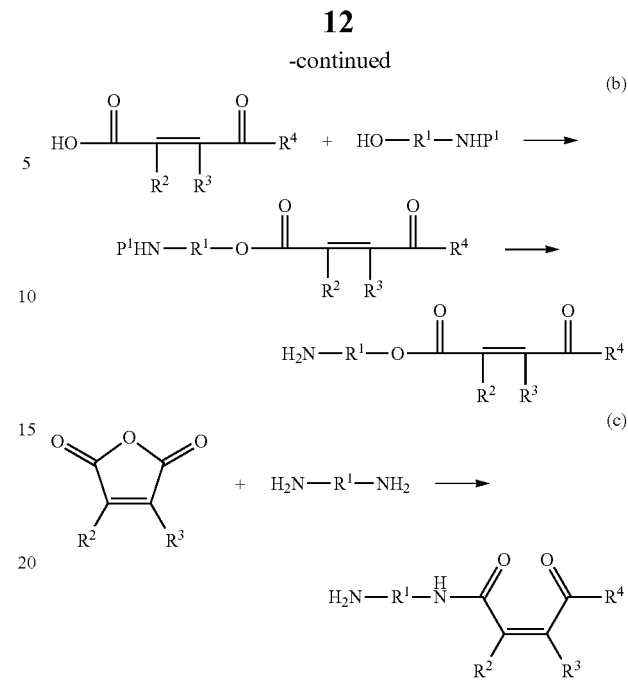

(in formula (a), formula (b) and formula (c), $R^1$, $R^2$, $R^3$ and $R^4$ are each as described above. $P^1$ represents a protective group.).

The protective group in $P^1$ includes a tert-butoxycarbonyl group and the like. In the case of use of a protective group, the protective group can be removed by a general method.

The compound represented by formula (II) can be produced by subjecting the corresponding acid anhydride such as maleic anhydride to an esterification reaction, an amidation reaction or a salt-forming reaction.

<Method for Producing Salt of Compound (I)>

The salt of a compound (I) can be produced, for example, by producing a compound (I) in which $R^4$ is a hydroxy group by reactions represented by formula (a), formula (b) and formula (c), and subjecting the compound (I) to a salt-forming reaction. The salt-forming reaction includes, for example, a reaction of forming a metal salt of the compound (I) using a metal.

<Method for Producing Salt Represented by Formula (III)>

The salt represented by formula (III) can be produced, for example, by a method represented by the following formula.

<Method for Producing Compound (I)>

The compound (I) can be produced, for example, by conducting reactions represented by formula (a), formula (b) and formula (c).

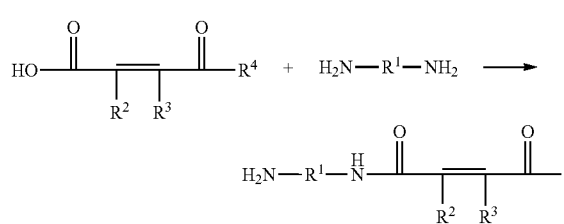

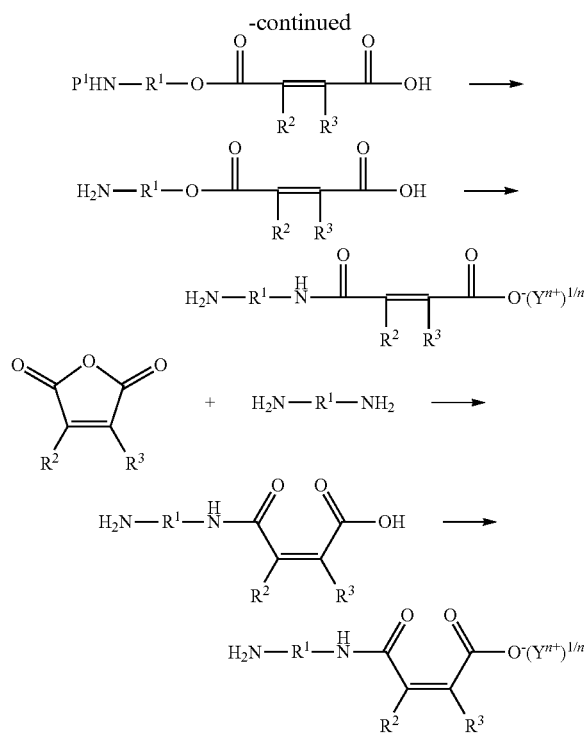

(wherein, $R^1$, $R^2$, $R^3$ and Y are each as described above. $P^1$ represents a protective group.).

The protective group in $P^1$ includes a tert-butoxycarbonyl group and the like. In the case of use of a protective group, the protective group can be removed by a general method.

The salt represented by formula (III) can be produced, for example, by producing a compound (I) in which $R^4$ is a hydroxy group by reactions represented by formula (a), formula (b) and formula (c), and subjecting the compound (I) to a salt-forming reaction. The salt-forming reaction includes a reaction of forming a metal salt of the compound (I) using a metal (hydroxides, carbonates and bicarbonates containing a metal represented by the above-described Y, and the like), and a reaction of forming a salt using organic bases capable of forming a salt with a carboxy group such as amines.

<Method for Producing Hydrate of Compound (I)>

The hydrate of a compound (I) can be produced, for example, by conducting reactions represented by formula (a), formula (b) and formula (c) in a mixed solvent of water and an organic solvent, or by producing a compound (I), then, conducting repulping or recrystallization with a water solvent.

<Method for Producing Methanol Solvate of Compound (I)>

The methanol solvate of a compound (I) can be produced, for example, by conducting reactions represented by formula (a), formula (b) and formula (c) in an organic solvent containing methanol, or by producing a compound (I), then, conducting repulping or recrystallization with a methanol solvent.

<Method for Producing Hydrate of Salt of Compound (I)>

The hydrate of a salt of a compound (I) can be produced, for example, by producing a compound (I) in which $R^4$ is a hydroxy group by reactions represented by formula (a), formula (b) and formula (c), and subjecting the compound (I) to a salt-forming reaction in a mixed solvent of water and an organic solvent, or by producing a salt of a compound (I), then, conducting repulping or recrystallization with a water solvent.

<Method for Producing Methanol Solvate of Salt of Compound (I)>

The methanol solvate of a salt of a compound (I) can be produced, for example, by producing a compound (I) in which $R^4$ is a hydroxy group by reactions represented by formula (a), formula (b) and formula (c), and subjecting the compound (I) to a salt-forming reaction in an organic solvent containing methanol, or by producing a salt of a compound (I), then, conducting repulping or recrystallization with a methanol solvent.

The rubber composition of the present invention is obtained by kneading at least one selected from the group consisting of (A1), (B1), (C1) and (D1), a rubber component and a filler. It is preferable to knead a sulfur component, it is more preferable to further knead a vulcanization accelerator and zinc oxide, together with the above-described components.

(A1), (B1), (C1) and (D1) may be any of a compound containing an E-configured compound (I), a compound containing a Z-configured compound (I) or a mixture of an E-configured compound and a Z-configured compound.

The rubber component includes natural rubber, epoxidated natural rubber, deproteinized natural rubber and other modified natural rubbers, and additionally exemplified are various synthetic rubbers such as polyisoprene rubber (IR), styrene-butadiene copolymerized rubber (SBR), polybutadiene rubber (BR), acrylonitrile-butadiene copolymerized rubber (NBR), isoprene-isobutylene copolymerized rubber (IIR), ethylene-propylene-diene copolymerized rubber (EPDM) and halogenated butyl rubber (HR), and highly unsaturated rubbers such as natural rubber, styrene-butadiene copolymerized rubber and polybutadiene rubber are preferably used. Natural rubber is particularly preferable. Further, it is effective to combine several types of rubber components, such as a combination of natural rubber and styrene-butadiene copolymerized rubber and a combination of natural rubber and polybutadiene rubber.

Examples of the natural rubber include natural rubbers of grades such as RSS#1, RSS#3, TSR20 and SIR20. As the epoxidated natural rubber, those having a degree of epoxidation of 10 to 60% by mol are preferable, and, for example, ENR25 and ENR50 manufactured by kun Poulenc Guthrie Inc. are exemplified. As the deproteinized natural rubber, deproteinized natural rubbers having a total nitrogen content of 0.3% by weight or less are preferable. As the modified natural rubber, modified natural rubbers containing a polar group obtained by previously reacting 4-vinylpyridine, N,N,-dialkylaminoethyl acrylate (for example, N,N,-diethylaminoethyl acrylate), 2-hydroxy acrylate and the like with natural rubber are preferably used.

Examples of SBR include emulsion polymerized SBRs and solution polymerized SBRs described in "Rubber Industry Handbook <fourth edition>", pp. 210 to 211, edited by The Society of Rubber Science and Technology, Japan. Especially, solution polymerized SBRs are preferably used as the rubber composition for tread, and further, particularly preferably used are commercially marketed products of solution polymerized SBRs such as "Nipol (registered trademark) NS116" manufactured by ZEON Corporation having a molecular end modified using 4,4'-bis(dialkylamino)benzophenone, solution polymerized SBRs such as "SL574" manufactured by JSR Corporation having a molecular end modified using a halogenated tin compound and silane-modified solution polymerized SBRs such as "E10" and "E15" manufactured by Asahi Kasei Corporation, and solution polymerized SBRs having any of nitrogen, tin and silicon or a combination thereof at the molecular end obtained by using singly any of a lactam compound, an amide compound, a urea-based compound, an N,N-dialkylacrylamide compound, an isocyanate compound, an imide compound, a silane compound having an alkoxy group (a trialkoxysilane compound and the like) and an aminosilane compound or by using two or more of the above-described several different compounds such as a tin compound and a silane compound having an alkoxy group and an alkylacrylamide compound and a silane compound having an alkoxy group and modifying the end thereof. Further, oil-extended SBRs obtained by adding an oil such as a process oil and an aroma oil to emulsion polymerized SBR and solution polymerized SBR after polymerization can be preferably used as the rubber composition for tread, and the like.

As examples of BR, solution polymerized BRs such as high cis BRs having a cis 1,4 linkage content of 90% or more and low cis BRs having a cis linkage content of around 35% are exemplified, and low cis BRs having a high vinyl content are preferably used. Further, particularly preferably used are tin-modified BRs such as "Nipol (registered trademark) BR 1250H" manufactured by ZEON Corporation, and solution polymerized BRs having any of nitrogen, tin and silicon or a combination thereof at the molecular end obtained by using singly any of 4,4'-bis(dialkylamino)benzophenone, a halogenated tin compound, a lactam compound, an amide compound, a urea-based compound, an N,N-dialkylacrylamide compound, an isocyanate compound, an imide compound, a silane compound having an alkoxy group (trialkoxysilane compound and the like) and an aminosilane compound or by using two or more of the above-described several different compounds such as a tin compound and a silane compound having an alkoxy group and an alkylacrylamide compound and a silane compound having an alkoxy group and modifying the end thereof. These BRs can be preferably used as the rubber composition for tread and the rubber composition for side wall, and usually used in a blend with SBR and/or natural rubber. Regarding the blending ratio, it is preferable for the rubber composition for tread that the content of SBR and/or natural rubber is 60 to 100% by weight and the content of BR is 40 to 0% by weight with respect to the total rubber weight, it is preferable for the rubber composition for side wall that the content of SBR and/or natural rubber is 10 to 70% by weight and the content of BR is 90 to 30% by weight with respect to the total rubber weight, and further, a blend having a content of natural rubber of 40 to 60% by weight and a content of BR of 60 to 40% by weight with respect to the total rubber weight is particularly preferable. In this case, a blend of modified SBR and non-modified SBR, and a blend of modified BR and non-modified BR are also preferable.

As the filler, exemplified are carbon black, silica, talc, clay, aluminum hydroxide, titanium oxide and the like usually used in the field of rubber, and carbon black and silica are preferably used, and further, carbon black is particularly preferably used. The carbon black includes, for example, those described in "Rubber Industry Handbook <Fourth edition>" p. 494, edited by The Society of Rubber Science and Technology, Japan, and preferable are carbon blacks such as HAF (High Abrasion Furnace), SAF (Super Abrasion Furnace), ISAF (Intermediate SAF), ISAF-HM (Intermediate SAF-High Modulus), FEF (Fast Extrusion Furnace), MAF, GPF (General Purpose Furnace) and SRF (Semi-Reinforcing Furnace). For the rubber composition for tire tread, carbon blacks having a CTAB surface area of 40 to 250 m$^2$/g, a nitrogen adsorption specific surface area of 20 to 200 m$^2$/g and a particle size of 10 to 50 nm are preferably used, carbon blacks having a CTAB surface area of 70 to 180 m$^2$/g are further preferable, and examples thereof include N110, N220, N234, N299, N326, N330, N330T, N339, N343, N351 and the like according to the standard of ASTM. Also preferable are surface-treated carbon blacks prepared by adsorbing silica to the surface of carbon black in an amount of 0.1 to 50% by weight. Further, it is effective to combine several kinds of fillers such as a combination of carbon black and silica, and it is preferable for the rubber composition for tire tread that carbon black is used singly or both carbon black and silica are used. For the rubber composition for carcass or side wall, carbon blacks having a CTAB surface area of 20 to 60 m$^2$/g and a particle size of 40 to 100 nm are preferably used, and examples thereof include N330, N339, N343, N351, N550, N568, N582, N630, N642, N660, N662, N754, N762 and the like according to the standard of ASTM. Though the use amount of such a filler is not particularly restricted, the use amount is preferably in the range of 5 to 100 parts by weight with respect to 100 parts by weight of a rubber component. When only carbon black is used as the filler, it is particularly preferably 30 to 80 parts by weight, and when carbon black is used together with silica in a tread member application, it is particularly preferably 5 to 50 parts by weight.

As the silica, silicas having a CTAB specific surface area of 50 to 180 m$^2$/g and silicas having a nitrogen adsorption specific surface area of 50 to 300 m$^2$/g are exemplified, and preferably used are commercially available products such as "AQ" and "AQ-N" manufactured by Tosoh Silica Corporation, "Ultrasil (registered trademark) VN3", "Ultrasil (registered trademark) VN3-G", "Ultrasil (registered trademark) 360" and "Ultrasil (registered trademark) 7000" manufactured by Degussa, "Zeosil (registered trademark) 115GR", "Zeosil (registered trademark) 1115 MP", "Zeosil (registered trademark) 1205 MP" and "Zeosil (registered trademark) Z85MP" manufactured by Rhodia and "Nipsil (registered trademark) AQ" manufactured by Nippon Silica Industrial Co., Ltd. It is also preferable to blend silicas having a pH of 6 to 8, silicas containing sodium in an amount of 0.2 to 1.5% by weight, spherical silicas having a roundness of 1 to 1.3, silicas surface-treated with a silicone oil such as dimethylsilicone oil, an organosilicon compound containing an ethoxysilyl group or an alcohol such as ethanol and polyethylene glycol, or silicas having two or more different nitrogen adsorption specific surface areas.

Though the use amount of such a filler is not particularly restricted, silica is preferably used in the rubber composition for tread for automobile, and the use amount thereof is preferably in the range of 10 to 120 parts by weight with respect to 100 parts by weight of a rubber component. When silica is blended, it is preferable to blend carbon black in an amount of 5 to 50 parts by weight, and the blending ratio of silica/carbon black is particularly preferably 0.7/1 to 1/0.1. When silica is usually used as the filler, it is preferable to add a compound having an element such as silicon or a functional group such as alkoxysilane capable of bonding to silica, such as one or more silane coupling agents selected from the group consisting of bis(3-triethoxysilylpropyl)tetrasulfide (manufactured by Degussa, "Si-69"), bis(3-triethoxysilylpropyl)disulfide (manufactured by Degussa, "Si-75"), bis(3-diethoxymethylsilylpropyl)tetrasulfide, bis(3-diethoxymethylsilylpropyl) disulfide, octanethioic acid S-[3-(triethoxysilyl)propyl]ester (manufactured by General Electronic Silicones, "NXT silane"), octanethioic acid S-[3-{(2-methyl-1,3-propanedialkoxy)ethoxysilyl}propyl]ester and octanethioic acid S-[3-{(2-methyl-1,3-propanedialkoxy)methylsilyl}propyl]ester phenyltriethoxysilane, methyltrimethoxysilane, methyltriethoxysilane, methyltriacetoxysilane, methyltributoxysilane, ethyltrimethoxysilae, ethyltriethoxysilane, isobutyltrimethoxysilane, isobutyltriethoxysilane, n-octyltrimethoxysilane, n-octyltriethoxysilane, vinyltrimethoxysilane, vinyltriethoxysilane, vinyltri(methoxyethoxy)silane, phenyltrimethoxysilane, phenyltriethoxysilane, phenyltriacetoxysilane, 3-methacryloxypropyltrimethoxysilane, 3-methacryloxypropyltriethoxysilane, 3-aminopropyltrimethoxysilane, 3-aminopropyltriethoxysilane, N-(2-aminoethyl)-3-aminopropyltrimethoxysilane, N-(2-aminoethyl)-3-aminopropyltriethoxysilane, (3-glycidoxypropyl)trimethoxysilane, (3-glycidoxypropyl)triethoxysilae, 2-(3,4-epoxycyclohexyl)ethyltrimethoxysilane, 2-(3,4-epoxycyclohexyl)ethyltriethoxysilane, 3-isocyanate propyltrimethoxysilane and 3-isocyanate propyltriethoxysilane, and particularly preferable are bis(3-triethoxysilylpropyl)tetrasulfide (manufactured by Degussa, "Si-69"), bis(3-triethoxysilylpropyl)disulfide (manufactured by Degussa, "Si-75") and 3-octanoylthiopropyltriethoxysilane (manufactured by General Electronic Silicones, "NXT silane"). Though the addition period of these compounds is not particularly restricted, it is preferable to blend these compounds into rubber simultaneously with silica, and the blending amount is preferably 2 to 10% by weight, further preferably 7 to 9% by weight with respect to silica. The blending temperature in blending is preferably in the range of 80 to 200° C., further preferably 110 to 180° C. Further, when silica is used as the filler, it is also preferable to blend a mono-hydric alcohol such as ethanol, butanol and octanol, a di- or mono-hydric alcohol such as ethylene glycol, diethylene glycol, triethylene glycol, polyethylene glycol, polypropylene glycol, pentaerythritol and polyether polyol, an N-alkylamine, an amino acid, or a liquid polybutadiene having a carboxyl-modified or amine-modified molecular end, and the like, in addition to silica and a compound having an element such as silicon or a functional group such as alkoxysilane capable of bonding to silica.

As the aluminum hydroxide, exemplified are aluminum hydroxides having a nitrogen adsorption specific surface area of 5 to 250 m$^2$/g and a DOP oiling quantity of 50 to 100 ml/100 g.

The sulfur component includes powdered sulfur, precipitated sulfur, colloidal sulfur, insoluble sulfur, highly-dispersible sulfur and the like. Usually, powdered sulfur is preferable, and in the case of use in a tire member having high sulfur content such as a member for belt, insoluble sulfur is preferable.

Examples of the vulcanization accelerator includes thiazole vulcanization accelerators, sulfenamide vulcanization accelerators and guanidine vulcanization accelerators described in Rubber Industry Handbook <Fourth edition> pp. 412 to 413 (published by The Society of Rubber Science and Technology, Japan on Jan. 20, 1994).

Specific examples thereof include N-cyclohexyl-2-benzothiazolyl sulfenamide (CBS), N-tert-butyl-2-benzothiazolyl sulfonamide (BBS), N,N-dicyclohexyl-2-benzothiazolyl sulfenamide (DCBS), 2-mercaptobenzothiazole (MBT), dibenzothiazyl disulfide (MBTS) and diphenylguanidine (DPG). In the case of use of carbon black as the filler, it is preferable to use N-cyclohexyl-2-benzothiazolyl sulfenamide (CBS), N-tert-butyl-2-benzothiazolyl sulfonamide (BBS), N,N-dicyclohexyl-2-benzothiazolyl sulfenamide (DCBS) or dibenzothiazyl disulfide (MBTS) and diphenylguanidine (DPG) together, and when silica and carbon black are used together as the filler, it is preferable to use any of N-cyclohexyl-2-benzothiazolyl sulfenamide (CBS), N-tert-butyl-2-benzothiazolyl sulfonamide (BBS), N,N-dicyclohexyl-2-benzothiazolyl sulfenamide (DCBS) and dibenzothiazyl disulfide (MBTS), and diphenylguanidine (DPG) together.

Though the ratio of sulfur to a vulcanization accelerator is not particularly restricted, the sulfur/vulcanization accelerator ratio is preferably in the range of 2/1 to 1/2 by weight. EV vulcanization in which the sulfur/vulcanization accelerator ratio is controlled to 1 or less as a method of improving the heat resistance of a rubber member composed mainly of natural rubber is preferably used also in the present invention in applications particularly needing an improvement in heat resistance.

Procedures of kneading components include a procedure of kneading a rubber component and a filler (hereinafter, referred to as "procedure 1" in some cases), and a procedure of, after that, kneading the composition obtained in the procedure 1 and a sulfur component (hereinafter, referred to as "procedure 2" in some cases). The compound (I) is blended in the procedure 1, in the procedure 2, or both in the procedure 1 and in the procedure 2. It is preferable that the compound (I) is blended in the procedure 1. Both the kneaded material obtained in the procedure 1 and the kneaded material obtained in the procedure 2 are included in the rubber composition of the present invention.

The use amount of the compound (I) is preferably in the range of 0.1 to 10 parts by weight, more preferably in the range of 0.3 to 3 parts by weight with respect to 100 parts by weight of a rubber component. The blending temperature in blending in the procedure 1 is preferably in the range of 80 to 200° C., further preferably in the range of 110 to 180° C. The blending temperature in blending in the procedure 2 is preferably in the range of 50 to 100° C.

It is also possible to previously blend the compound (I) with a carrier. Such a carrier includes fillers exemplified above and "inorganic fillers and reinforcing agents" described in "Rubber Industry Handbook <fourth edition>", pp. 510 to 513 edited by The Society of Rubber Science and Technology, Japan. Carbon black, silica, calcined clay and aluminum hydroxide are preferable. Though the use amount of such a carrier is not particularly restricted, it is preferably in the range of 10 to 1000 parts by weight with respect to 100 parts by weight of a compound (I).

It is also possible to blend and knead agents improving the viscoelastic property conventionally used in the field of rubber. Such agents include, for example, N,N'-bis(2-methyl-2-nitropropyl)-1,6-hexanediamine (manufactured by Sumitomo Chemical Co., Ltd., "Sumifine (registered trademark) 1162"), dithiouracil compounds described in JP-A No. 63-23942, nitrosoquinoline compounds such as 5-nitroso-8-hydroxyquinoline (NQ-58) described in JP-A No. 60-82406, alkylphenol-sulfur chloride condensates described in JP-A No. 2009-138148 such as "Tackirol (registered trademark) AP, V-200" manufactured by Taoka Chemical Co., Ltd. and "Vultac 2, 3, 4, 5, 7, 710" manufactured by Pennwalt Corp., bis(3-triethoxysilylpropyl)tetrasulfide (manufactured by Degussa, "Si-69"), bis(3-triethoxysilylpropyl)disulfide (manufactured by Degussa, "Si-75"), bis(3-diethoxymethylsilylpropyl) tetrasulfide, bis(3-diethoxymethylsilylpropyl) disulfide, octanethioic acid S-[3-(triethoxysilyl)propyl]ester, octanethioic acid S-[3-{(2-methyl-1,3-propanedialkoxy)ethoxysilyl}propyl]ester, and silane coupling agents such as octanethioic acid S-[3-{(2-methyl-1,3-propanedialkoxy)methylsilyl}propyl]ester phenyltriethoxysilane, methyltrimethoxysilane, methyltriethoxysilane, methyltriacetoxysilane, methyltributoxysilane, ethyltrimethoxysilane, ethyltriethoxysilane, isobutyltrimethoxysilane, isobutyltriethoxysilane, n-octyltrimrmethoxysilanre, n-octyltriethoxysilane, vinyltrimethoxysilane, vinyltriethoxysilane, vinyltri(methoxyethoxy)silane, phenyltrimethoxysilane, phenyltriethoxysilane, phenyltriacetoxysilane, 3-methacryloxypropyltrimethoxysilane, 3-methacryloxypropyltriethoxysilane, 3-aminopropyltrimethoxysilane, 3-aminopropyltriethoxysilane, N-(2-aminoethyl)-3-aminopropyltrimethoxysilane, N-(2-aminoethyl)-3-aminopropyltriethoxysilane, (3-glycidoxypropyl)trimethoxysilane, (3-glycidoxypropyl)triethoxysilane, 2-(3,4-epoxycyclohexyl)ethyltrimethoxysilane, 2-(3,4-epoxycyclohexyl)ethyltriethoxysilane, 3-isocyanate propyltrimethoxysilane, 3-isocyanate propyltriethoxysilane and the like, 1,6-bis(N,N'-dibenzylthiocarbamoyldithio)hexane (manufactured by Beyer, "KA9188"), 1,6-hexamethylene dithiosulfate disodium salt dihydrate, 1,3-bis(citraconimidemethyl)benzene (manufactured by Flexsys, "Perkalink 900"), 1-benzoyl-2-phenylhydrazide, carboxylic acid hydrazide derivatives such as 1- or 3-hydroxy-N'-(1-methylethylidene)-2-naphthoic acid hydrazide, and 1- or 3-hydroxy-N'-(1-methylpropylidene)-2-naphthoic acid hydrazide, 1- or 3-hydroxy-N'-(1,3-dimethylbutylidene)-2-naphthoic acid hydrazide and 1- or 3-hydroxy-N'-(2-furylmethylene)-2-naphthoic acid hydrazide and the like described in JP-A No. 2004-91505, 3-hydroxy-N'-(1,3-dimethylbutylidene)-2-naphthoic acid hydrazide, 3-hydroxy-N'-(1,3-diphenylethylidene)-2-naphthoic acid hydrazide and 3-hydroxy-N'-(1-methylethylidene)-2-naphthoic acid hydrazide described in JP-A No. 2000-190704, bismercapto-oxadiazole compounds described in JP-A No. 2006-328310, pyrithione salt compounds described in JP-A No. 2009-40898, and cobalt hydroxide compounds described in JP-A No. 2006-249361.

Of them, preferable are N,N'-bis(2-methyl-2-nitropropyl)-1,6-hexanediamine (manufactured by Sumitomo Chemical Co., Ltd., "Sumifine (registered trademark) 1162"), 5-nitroso-8-hydroxyquinoline (NQ-58), bis(3-triethoxysilylpropyl)tetrasulfide (manufactured by Degussa, "Si-69"), bis(3-triethoxysilylpropyl)disulfide (manufactured by Degussa, "Si-75"), 1,6-bis(N,N'-dibenzylthiocarbamoyldithio)-hexane (manufactured by Beyer, "KA9188"), hexamethylene bisthiosulfate disodium salt dihydrate, 1,3-bis(citraconimidemethyl)benzene (manufactured by Flexsys, "Perkalink 900"), and alkylphenol-sulfur chloride condensates such as "Tackirol (registered trademark) AP, V-200" manufactured by Taoka Chemical Co., Ltd.

In blending zinc oxide, blending in the procedure 1 is preferable, and in blending a vulcanization accelerator, blending in the procedure 2 is preferable, respectively.

It is also possible to blend and knead various compounding agents conventionally used in the field of rubber. Such compounding agents include, for example, antioxidants such as "Antigen (registered trademark) 6C" manufactured by Sumitomo Chemical Co., Ltd.; oils; fatty acids such as stearic acid; coumarone-indene resins such as a coumarone resin NG4 (softening point: 81 to 100° C.) manufactured by Nippon Steel Chemical Co., Ltd. and Process Resin AC5 (softening point: 75° C.) manufactured by Kobe Oil Chemical Industrial Co., Ltd.; terpene type resins such as terpene resins, terpene-phenol resins and aromatic modified terpene resins; rosin derivatives such as "Nikanol (registered trademark) A70" (softening point: 70 to 90° C.) manufactured by Mitsubishi Gas Chemical Company, Inc.; hydrogenated rosin derivatives; novolac type alkylphenol resins; resol type alkylphenol resins; C5 type petroleum resins; and liquid polybutadiene. These compounding agents can be blended by any of the procedure 1 and the procedure 2.

The above-described oil includes process oils, vegetable fats and oils and the like. The process oil includes paraffinic process oils, naphthenic process oils, aromatic process oils and the like, for example, an aromatic oil (manufactured byCOSMO OIL Co., Ltd., "NC-140"), a process oil (manufactured by Idemitsu Kosan Co., Ltd., "Diana Process PS32") and the like.

The above-described antioxidant includes, for example, those described in "Rubber Industry Handbook <Fourth edition>", pp. 436 to 443 edited by The Society of Rubber Science and Technology, Japan. Of them, N-phenyl-N'-1,3-dimethylbutyl-p-phenylenediamine (6PPD), a reaction product of aniline and acetone (TMDQ), poly(2,2,4-trimethyl-1,2-)dihydroquinoline) (manufactured by Matsubara Sangyo, "Antioxidant FR"), synthetic waxes (paraffin waxes and the like) and vegetable waxes are preferably used.

The wax includes "Sannoc (registered trademark) wax" manufactured by Ouchi Shinko Chemical Industrial Co., Ltd., "OZOACE-0355" manufactured by Nippon Seiro Co., Ltd., and the like.

It is also possible to blend and knead vulcanizing agents such as morpholine disulfide conventionally used in the field of rubber. It is preferable that these are blended in the procedure 2.

Further, a peptizer and a retarder may be blended and kneaded, furthermore, general various rubber chemicals and softening agents and the like may be blended and kneaded if necessary.

As the retarder, exemplified are phthalic anhydride, benzoic acid, salicylic acid, N-nitrosodiphenylamine, N-(cyclohexylthio)-phthalimide (CTP), sulfonamide derivatives, diphenylurea, bis(tridecyl)pentaerythritol-diphosphite and the like, and N-(cyclohexylthio)-phthalimide (CTP) is preferably used.

Though the retarder may be blended and kneaded in the procedure 1, it is preferable to blend and knead the retarder in the procedure 2.

Though the use amount of the retarder is not particularly restricted, it is preferably in the rage of 0.01 to 1 part by weight, particularly preferably in the range of 0.05 to 0.5 parts by weight with respect to 100 parts by weight of a rubber component.

The temperature in the procedure 1 is preferably 80 to 200° C., more preferably 110 to 180° C. The temperature in the procedure 2 is preferably 50 to 100° C.

The vulcanized rubber of the present invention is obtained by thermally treating the rubber composition obtained in the procedure 2 (namely, a rubber composition obtained by kneading a compound (I), a rubber component, a filler and a sulfur component, hereinafter, referred to as "the rubber composition" in some cases.).

The temperature in the thermal treatment is preferably 110 to 180° C. The thermal treatment is usually carried out under normal pressure or increased pressure.

The vulcanized rubber of the present invention includes vulcanized rubber obtained by thermally treating the rubber composition processed into a particular condition.

Here, "the rubber composition processed into a particular condition" includes, for example, "the rubber composition coated by a steel cord", "the rubber composition coated by a carcass fiber cord", "the rubber composition processed into the shape of a member for tread" and the like in the field of rubber. Members such as belts, carcasses, inner liners, side walls and treads (cap tread or under tread) obtained by thermal treatment are usually further molded into the shape of a tire together with other members by a method usually conducted in the field of tire, that is, the rubber composition is incorporated into a tire, and a green tire containing the rubber composition is thermally treated. Such a thermal treatment is usually conducted under increased pressure.

As the rubber component in a rubber compounding suitable for tread members suitable for tires of trucks, buses, light trucks and construction large tires, preferable is a natural rubber single body or a blend composed of natural rubber as the main component and SBR and/or BR. As the filler, a carbon black single body or a blend composed of silica as the main component and carbon black is preferably used. Further, it is preferable to use concurrently a viscoelasticity improving agent such as N,N'-bis(2-methyl-2-nitropropyl)-1,6-hexanediamine (manufactured by Sumitomo Chemical Co., Ltd., "Sumifine (registered trademark) 1162"), 5-nitroso-8-hydroxyquinoline (NQ-58), bis(3-triethoxysilylpropyl)tetrasulfide (Si-69), bis(3-triethoxysilylpropyl)disulfide (Si-75), 1,6-bis(N,N'-dibenzylthiocarbamoyldithio)-hexane (manufactured by Beyer, "KA9188"), hexamethylene bisthiosulfate disodium salt dihydrate, 1,3-bis(citraconimidemethyl)benzene (manufactured by Flexsys, "Perkalink 900"), alkylphenol-sulfur chloride condensates such as "Tackirol (registered trademark) AP, V-200" manufactured by Taoka Chemical Co., Ltd., etc.

As the rubber component in a rubber compounding suitable for tread members suitable for passenger car tires, preferable is a solution polymerized SBR single body having a molecular end modified with a silicon compound or a blend composed of the above-described end-modified solution polymerized SBR as the main component and at least one rubber selected from the group consisting of non-modified solution polymerized SBR, emulsion polymerized SBR, natural rubber and BR. As the filler, a blend composed of silica as the main component and carbon black is preferably used. Further, it is preferable to use concurrently a viscoelasticity improving agent such as N,N'-bis(2-methyl-2-nitropropyl)-1,6-hexanediamine (manufactured by Sumitomo Chemical Co., Ltd., "Sumifine (registered trademark) 1162"), 5-nitroso-8-hydroxyquinoline (NQ-58), bis(3-triethoxysilylpropyl)tetrasulfide (Si-69), bis(3-triethoxysilylpropyl)disulfide (Si-75), 1,6-bis(N,N'-dibenzylthiocarbamoyldithio)-hexane (manufactured by Beyer, "KA9188"), hexamethylene bisthiosulfate disodium salt dihydrate, 1,3-bis(citraconimidemethyl)benzene (manufactured by Flexsys, "Perkalink 900"), alkylphenol-sulfur chloride condensates such as "Tackirol (registered trademark) AP, V-200" manufactured by Taoka Chemical Co., Ltd., etc.

As the rubber component in a rubber compounding suitable for side wall members, preferable is a blend composed of BR as the main component and at least one rubber selected from the group consisting of non-modified solution polymerized SBR, emulsion polymerized SBR and natural rubber. As the filler, a carbon black single body or a blend composed of carbon black as the main component and silica is preferably used. Further, it is preferable to use concurrently a viscoelasticity improving agent such as N,N'-bis(2-methyl-2-nitropropyl)-1,6-hexanediamine (manufactured by Sumitomo Chemical Co., Ltd., "Sumifine (registered trademark) 1162"), 5-nitroso-8-hydroxyquinoline (NQ-58), bis(3-triethoxysilylpropyl)tetrasulfide (Si-69), bis(3-triethoxysilylpropyl)disulfide (Si-75), 1,6-bis(N,N'-dibenzylthiocarbamoyldithio)-hexane (manufactured by Beyer, "KA9188"), hexamethylene bisthiosulfate disodium salt dihydrate, 1,3-bis(citraconimidemethyl)benzene (manufactured by Flexsys, "Perkalink 900"), alkylphenol-sulfur chloride condensates such as "Tackirol (registered trademark) AP, V-200" manufactured by Taoka Chemical Co., Ltd., etc.

As the rubber component in a rubber compounding suitable for carcass and belt members, preferable is a natural rubber single body or a blend composed of natural rubber as the main component and BR. As the filler, a carbon black single body or a blend composed of carbon black as the main component and silica is preferably used. Further, it is preferable to use concurrently a viscoelasticity improving agent such as N,N'-bis(2-methyl-2-nitropropyl)-1,6-hexanediamine (manufactured by Sumitomo Chemical Co., Ltd., "Sumifine (registered trademark) 1162"), 5-nitroso-8-hydroxyquinoline (NQ-58), bis(3-triethoxysilylpropyl)tetrasulfide (Si-69), bis(3-triethoxysilylpropyl)disulfide (Si-75), 1,6-bis(N,N'-dibenzylthiocarbamoyldithio)-hexane (manufactured by Beyer, "KA9188"), hexamethylene bisthiosulfate disodium salt dihydrate, 1,3-bis(citraconimidemethyl)benzene (manufactured by Flexsys, "Perkalink 900"), alkylphenol-sulfur chloride condensates such as "Tackirol (registered trademark) AP, V-200" manufactured by Taoka Chemical Co., Ltd., etc.

Using thus obtainable vulcanized rubber, a tire is produced by a usual method. That is, the above-described rubber composition at a stage before a vulcanization treatment is extrusion-processed into a member for tread, and pasting-molded on a tire molding machine by a usual method to form a green tire, and this green tire is heated and pressed in a vulcanizer to obtain a tire. The tire includes, for example, pneumatic tires, solid tires and the like.

The fuel consumption of a car installed with thus obtainable tire improves, and lowering of fuel consumption can be attained.

When the compound (I) is added to a rubber composition for tire, the viscoelastic property of vulcanized rubber obtained by vulcanizing the rubber composition can be improved. The vulcanized rubber can be used not only in the above-described tire application but also in various vibration-proof rubber applications, various rubber belt applications, a damping material application and a seismic isolation rubber application. Such vibration-proof rubber includes, for example, automobile vibration-proof rubbers for an engine mount, a strut mount, a bush, an exhaust hanger and the like. The vibration-proof rubber is usually obtained by processing a kneaded material into the shape of the vibration-proof rubber, then, thermally treating this. The rubber belt application includes, for example, a transmission belt, a conveyer belt, a V belt and the like.

EXAMPLES

The present invention will be explained specifically using examples, test examples, production examples and the like mentioned below, but the present invention is not limited to them.

Production Example 1

Production of (2Z)-4-[(4-aminophenyl)amino]-4-oxo-2-butenoic acid

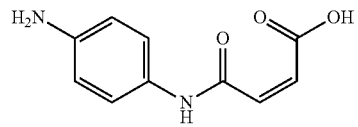 [SMILES: Nc1ccc(NC(=O)/C=C\C(=O)O)cc1]

Under a nitrogen atmosphere, into a reaction vessel were charged 25.17 g (0.233 mol) of 1,4-phenylenediamine and 230 ml of tetrahydrofuran. A solution prepared by dissolving 22.84 g (0.233 mol) of maleic anhydride in 50 ml of tetrahydrofuran was dropped into this under cooling with ice over a period of about 1 hour, then, the mixture was stirred at room temperature overnight. After completion of the reaction, the deposited crystal was isolated by filtration, washed twice with 40 ml of tetrahydrofuran, dried at 40° C. for 5 hours, to obtain 46.92 g of coarse (2Z)-4-[(4-aminophenyl)amino]-4-oxo-2-butenoic acid as an orange powder. To 46.92 g of coarse (2Z)-4-[(4-aminophenyl)amino]-4-oxo-2-butenoic acid was added 250 ml of methanol, and the mixture was stirred at 50° C. for 1 hour and cooled, then, filtrated and washed twice with 20 ml of methanol. The resultant crystal was dried, to obtain 42.67 g of (2Z)-4-[(4-aminophenyl)amino]-4-oxo-2-butenoic acid as a yellow-orange powder. Yield: 88.8%.

Production Example 2

Production of (2Z)-4-[(4-aminophenyl)amino]-4-oxo-2-butenoic acid mono-hydrate

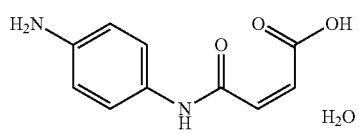

Under a nitrogen atmosphere, into a reaction vessel were charged 13.0 g (0.12 mol) of 1,4-phenylenediamine and 140 ml of tetrahydrofuran. A solution prepared by dissolving 11.77 g (0.12 mol) of maleic anhydride in 25 ml of tetrahydrofuran was dropped into this under cooling with ice over a period of about 1 hour, then, the mixture was stirred at room temperature overnight. After completion of the reaction, the deposited crystal was isolated by filtration, and dried to obtain 24.20 g of coarse (2Z)-4-[(4-aminophenyl)amino]-4-oxo-2-butenoic acid as an orange powder. To 24.2 g of coarse (2Z)-4-[(4-aminophenyl)amino]-4-oxo-2-butenoic acid were added 250 ml of tetrahydrofuran and 50 ml of water, and the mixture was stirred at room temperature for 2 hours, then, isolated by filtration, and the filtrated material was washed twice with 20 ml of 50% tetrahydrofuran water. The resultant crystal was dried at 40° C. for 5 hours, to obtain 21.96 g of (2Z)-4-[(4-aminophenyl)amino]-4-oxo-2-butenoic acid mono-hydrate as a yellow-orange powder. Yield: 81.5%.

Production Example 3

Production of (2Z)-4-[(3-aminophenyl)amino]-4-oxo-2-butenoic acid

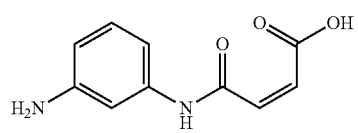 [SMILES: Nc1cccc(NC(=O)/C=C\C(=O)O)c1]

Under a nitrogen atmosphere, into a reaction vessel were charged 9.96 g (92 mmol) of 1,3-phenylenediamine and 250 ml of tetrahydrofuran. A solution prepared by dissolving 9.03 g (92 mmol) of maleic anhydride in 27 ml of tetrahydrofuran was dropped into this under cooling with ice over a period of about 1 hour, then, the mixture was stirred at room temperature overnight. After completion of the reaction, the deposited crystal was separated by filtration, and the filtrate was condensed to dryness, to obtain 16.68 g of coarse (2Z)-4-[(3-aminophenyl)amino]-4-oxo-2-butenoic acid. To 16.68 g of coarse (2Z)-4-[(3-aminophenyl)amino]-4-oxo-2-butenoic acid was added 450 ml of tetrahydrofuran, and the mixture was refluxed with heating for 1 hour, then, the deposited crystal was isolated by hot filtration, and dried to obtain 7.58 g of coarse ((Z)-3-(3-aminophenylcarbamoyl)acrylic acid. Further, to this crystal was added 30 ml of methanol, and the mixture was stirred at room temperature for 1 hour, then, the deposited crystal was isolated by filtration, and dried to obtain 6.94 g of (2Z)-4-[(3-aminophenyl)amino]-4-oxo-2-butenoic acid as a yellow-white solid. Yield: 36.5%.

Production Example 4

Production of (2Z)-4-[(4-aminophenyl)amino]-2-methyl4-oxo-2-butenoic acid

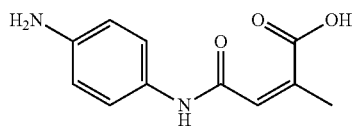

Under a nitrogen atmosphere, into a reaction vessel were charged 10.0 g (92.5 mmol) of 1,4-phenylenediamine and 250 ml of tetrahydrofuran. A solution prepared by dissolving 10.4 g (92.5 mmol) of citraconic anhydride in 20 ml of tetrahydrofuran was dropped into this under cooling with ice over a period of 20 minutes, then, the mixture was stirred at room temperature for 3 hours. After completion of the reaction, the deposited crystal was isolated by filtration, and dried to obtain 15 g of coarse (2Z)-4-[(4-aminophenyl)amino]-2-methyl4-oxo-2-butenoic acid. Five grams (5 g) of coarse (2Z)-4-[(4-aminophenyl)amino]-2-methyl4-oxo-2-butenoic acid was repulped with 2-propanol and methanol each at 50° C. for 3 hours, then, repulped with chloroform, to obtain 13.1 g of (2Z)-4-[(4-aminophenyl)amino]-2-methyl-4-oxo-2-butenoic acid as a yellow solid. Yield: 64.3%.

Production Example 5

Production of (2Z)-4-[(6-aminohexyl)amino]-4-oxo-2-butenoic acid

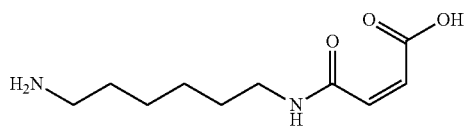 [SMILES: NCCCCCCNC(=O)/C=C\C(=O)O]

Under a nitrogen atmosphere, into a reaction vessel were charged 10.00 g (86.1 mmol) of 1,6-diaminchexane and 400 ml of tetrahydrofuran. A solution prepared by dissolving 8.44 g (86.1 mmol) of maleic anhydride in 25 ml of tetrahydrofuran was dropped into this under cooling with ice over a period of 2 hours, then, the mixture was stirred at room temperature overnight. After completion of the reaction, the deposited solid was isolated by filtration, and dried under reduced pressure. The resultant solid was dissolved in 100 ml of methanol, 100 ml of chloroform was added, and the solvent was distilled off under reduced pressure, the resultant solid was dried under reduced pressure at 35° C., to obtain 17 g of (2Z)-4-[(6-aminohexyl)amino]-4-oxo-2-butenoic acid as a white solid. NMR measurement thereof revealed a content of (2Z)-4-[(6-aminohexyl)amino]-4-oxo-2-butenoic acid of 38.4%. Net quantity: 8.1 g, yield: 43.9%.

Example 1

Production of (2Z)-4-[(4-aminophenyl)amino]-4-oxo-2-butenoic acid methanol solvate

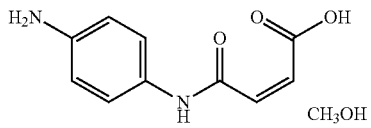

Under a nitrogen atmosphere, into a reaction vessel were charged 10.00 g (92.5 mmol) of 1,4-phenylenediamine and 80 ml of methanol. A solution prepared by dissolving 6.05 g (61.6 mmol) of maleic anhydride in 20 ml of tetrahydrofuran was dropped into this under cooling with ice over a period of 1 hour, then, the mixture was stirred at 0 to 10° C. for 3 hours. After completion of the reaction, the temperature thereof was raised to room temperature, the deposited solid was isolated by filtration, and washed with 50 ml of methanol. The resultant solid was dried under reduced pressure at 40° C., to obtain 12.63 g of (2Z)-4-[(4-aminophenyl)amino]-4-oxo-2-butenoic acid methanol solvate as a pale yellow powder. Yield: 86.0%. $H^1$-NMR (270 MHz, DMSO-d6) $\delta_{ppm}$: 10.6 (1H, s), 7.3 (2H, d, J=8.9 Hz), 6.5 (2H, d, J=8.9 Hz), 6.5 (1H, d, J=12.5 Hz), 6.3 (1H, d, J=12.2 Hz), 3.2 (3H, s).

Example 2

Production of sodium (2Z)-4-[(4-aminophenyl)amino]-4-oxo-2-butenoate

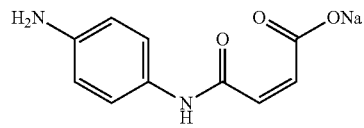

Under a nitrogen atmosphere, into a reaction vessel were charged 15.00 g (138.7 mmol) of 1,4-phenylenediamine and 255 ml of tetrahydrofuran. A solution prepared by dissolving 9.07 g (92.5 mmol) of maleic anhydride in 45 ml of tetrahydrofuran was dropped into this under cooling with ice over a period of about 3 hours, then, the mixture was stirred at room temperature overnight. After completion of the reaction, the deposited crystal was isolated by filtration, washed with 30 ml of tetrahydrofuran, and dried at 40° C. to obtain 18.14 g of coarse (2Z)-4-[(4-aminophenyl)amino]-4-oxo-2-butenoic acid as an orange powder. To 18.14 g of coarse (2Z)-4-[(4-aminophenyl)amino]-4-oxo-2-butenoic acid was added 36 ml of water and the mixture was cooled to 0 to 10° C., and 17.59 ml of a 5N sodium hydroxide aqueous solution was dropped. Thereafter, the solvent was distilled off under reduced pressure to obtain a residue to which 270 ml of ethanol was added, and the mixture was stirred at 70° C. for 1 hour, cooled down to room temperature, then, the solid was filtrated and washed twice with 25 ml of methanol. The resultant solid was dried at 45° C. for 2 hours, to obtain 16.2 g of sodium (2Z)-4-[(4-aminophenyl)amino]-4-oxo-2-butenoate as a pale brown-white powder. Yield: 76.8%
$H^1$-NMR (270 MHz, DSO-d6) $\delta_{ppm}$: 14.5 (1H, s), 7.3 (2H, d, J=8.9 Hz), 6.5 (2H, d, J=8.6 Hz), 6.1 (1H, d, J=13.5 Hz), 5.6 (1H, d, J=13.2 Hz), 4.8 (2H, s).

Example 3-1

Production of sodium (2Z)-4-[(4-aminophenyl)amino]-4-oxo-2-butenoate di-hydrate

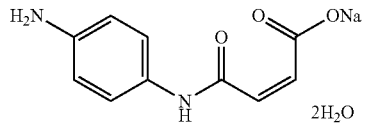

Under a nitrogen atmosphere, into a reaction vessel were charged 10.49 g (content: 86%, net quantity: 9.02 g (47.3 mmol)) of (2Z)-4-[(4-aminophenyl)amino]-4-oxo-2-butenoic acid and 30 ml of water. To this was added 47.3 ml (47.3 mmol) of a 1 mol/L sodium hydroxide aqueous solution. After completion of the reaction, the solution was condensed to dryness to obtain a solid to which 30 ml of tetrahydrofuran was added, and the mixture was stirred at room temperature for 30 minutes, then, the deposited crystal was isolated by filtration, and dried to obtain 11.28 g of sodium (2Z)-4-[(4-aminophenyl)amino]-4-oxo-2-butenoate di-hydrate as a yellow solid. Yield: 90%
$H^1$-NMR (270 MHz, DMSO-d6) $\delta_{ppm}$: 14.6 (1H, s), 7.3 (2H, d, J=8.9 Hz), 6.5 (2H, d, J=8.9 Hz), 6.1 (1H, d, J=13.5 Hz), 5.6 (1H, d, J=13.5 Hz), 4.8 (2H, s), 3.3 (4H, s)

Example 3-2

Production of sodium (2Z)-4-[(4-aminophenyl)amino]-4-oxo-2-butenoate di-hydrate

Under a nitrogen atmosphere, into a reaction vessel were charged 211.3 g (1.95 mol) of 1,4-phenylenediamine and 3900 ml of tetrahydrofuran. A solution prepared by dissolving 127.2 g (1.30 mol) of maleic anhydride in 600 ml of tetrahydrofuran was dropped into this under cooling with ice over a period of about 3.3 hours, then, the mixture was stirred at room temperature overnight. After completion of the reaction, the deposited crystal was isolated by filtration, washed twice with 280 ml of tetrahydrofuran, and dried to obtain 259.2 g of coarse (2Z)-4-[(4-aminophenyl)amino]-4-oxo-2-butenoic acid as a yellow-orange powder. To 259.2 g of coarse (2Z)-4-[(4-aminophenyl)amino]-4-oxo-2-butenoic acid was added 520 ml of water and the mixture was cooled to 0 to 10° C., and 237 ml of a 5N sodium hydroxide aqueous solution was dropped, then, 6.5 ml of a 1N sodium hydroxide aqueous solution was dropped. Thereafter, the solvent was distilled off under reduced pressure to obtain a residue to which 200 ml of 2-propanol was added, and the solvent was distilled off under reduced pressure again. To the resultant yellow-brown solid was added 800 ml of tetrahydrofuran and the mixture was stirred at room temperature overnight, the solid was isolated by filtration, and washed four times with 100 ml of tetrahydrofuran and dried at 45° C. for 5 hours, to obtain 297.7 g of sodium (2Z)-4-[(4-aminophenyl)amino]-4-oxo-2-butenoate di-hydrate as a yellow powder. Yield: 86.7%.
$H^1$-NMR (270 MHz, DMSO-d6) $\delta_{ppm}$: 14.6 (1H, s), 7.3 (2H, d, J=8.9 Hz), 6.5 (2H, d, J=8.9 Hz), 6.1 (1H, d, J=13.5 Hz), 5.6 (1H, d, J=13.5 Hz), 4.8 (2H, s), 3.3 (4H, s).

Example 4

Production of sodium (2Z)-4-[(4-aminophenyl)amino]-4-oxo-2-butenoate methanol solvate

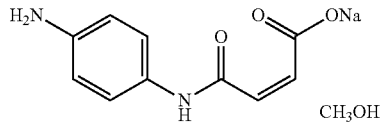

Under a nitrogen atmosphere, into a reaction vessel were charged 195.5 g (1.81 mol) of 1,4-phenylenediamine and 3000 ml of tetrahydrofuran. A solution prepared by dissolving 118.1 g (1.20 mol) of maleic anhydride in 1200 ml of tetrahydrofuran was dropped into this under cooling with ice over a period of about 3 hours, then, the mixture was stirred at room temperature overnight. After completion of the reaction, the deposited crystal was isolated by filtration, washed twice with 250 ml of tetrahydrofuran, and dried at 40° C. to obtain 241.8 g of coarse (2Z)-4-[(4-aminophenyl)amino]-4-oxo-2-butenoic acid as a yellow-orange powder. To 241.8 g of coarse (2Z)-4-[(4-aminophenyl)amino]-4-oxo-2-butenoic acid was added 484 ml of water, and the mixture was cooled to 0 to 10° C., and 216 ml of a 5N sodium hydroxide aqueous solution was dropped, then, 21 ml of a 1N sodium hydroxide aqueous solution was dropped. Thereafter, the solvent was distilled off under reduced pressure to obtain a residue to which 200 ml of 2-propanol was added, and the solvent was distilled off under reduced pressure again. To the resultant yellow-brown solid was added 800 ml of tetrahydrofuran, the mixture was stirred at room temperature overnight, and the solid was isolated by filtration, washed three times with 100 ml of tetrahydrofuran and dried, to obtain 279 g of coarse sodium (2Z)-4-[(4-aminophenyl)amino]-4-oxo-2-butenoate. Coarse sodium (2Z)-4-[(4-aminophenyl)amino]-4-oxo-2-butenoate (279 g) was bisected, 2800 ml of methanol was added to each portion, refluxed with heating for 1 hour, then, hot-filtrated to remove insoluble materials. The filtrates were condensed under reduced pressure, and the resultant solids were combined, 750 ml of tetrahydrofuran was added and the mixture was stirred at room temperature overnight, thermally insulated at 50° C. for 30 minutes, then, hot-filtrated. The resultant solid was washed three times with 150 ml of tetrahydrofuran, dried under reduced pressure at 45° C. for 5 hours, to obtain 264.6 g of sodium (2Z)-4-[(4-aminophenyl)amino]-4-oxo-2-butenoate methanol solvate as a pale brown-white powder. Yield: 84.5%.

$H^1$-NMR (300 MHz, DMSO-d6) $\delta_{p\,p\,m}$: 14.6 (1H, s), 7.3 (2H, d, J=8.9 Hz), 6.5 (2H, d, J=8.9 Hz), 6.1 (1H, d, J=13.5 Hz), 5.6 (1H, d, J=13.5 Hz), 4.1 (1H, q, J=5.4, 10.5 Hz), 4.8 (2H, s), 3.2 (3H, s).

Example 5

Production of potassium (2Z)-4-[(4-aminophenyl)amino]-4-oxo-2-butenoate mono-hydrate

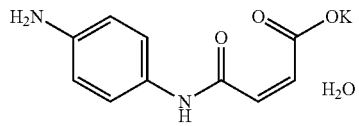

Under a nitrogen atmosphere, into a reaction vessel were charged 13.23 g (122.4 mmol) of 1,4-phenylenediamine and 225 ml of tetrahydrofuran. A solution prepared by dissolving 8.00 g (81.6 mmol) of maleic anhydride in 24 ml tetrahydrofuran was dropped into this under cooling with ice over a period of 2 hours, then, the mixture was stirred at room temperature for 3 hours. After completion of the reaction, 17.99 g (81.6 mmol) of a 25% potassium hydroxide aqueous solution was dropped under cooling with ice over a period of 30 minutes, and the mixture was stirred at room temperature for 2 hours. Thereafter, the solvent was distilled off under reduced pressure to obtain a residue to which 200 ml of tetrahydrofuran was added, and the mixture was stirred at 40° C. for 1 hour. After cooling to room temperature, the deposited solid was isolated by filtration, and washed with 50 ml of tetrahydrofuran. The resultant solid was dried under reduced pressure at 50° C. for 5 hours, to obtain 19.79 g of potassium (2Z)-4-[(4-aminophenyl)amino]-4-oxo-2-butenoate monohydrate as a red-brown solid. Yield: 92.5%

$H^1$-NMR (270 MHz, DMSO-d6) $\delta_{p\,p\,m}$: 14.8 (1H, s), 7.3 (2H, d, J=8.9 Hz), 6.5 (2H, d, J=8.9 Hz), 6.0 (1H, d, J=13.2 Hz), 5.6 (1H, d, J=13.5 Hz), 4.8 (2H, s), 3.3 (2H, s).

Example 6

Production of lithium (2Z)-4-[(4-aminophenyl)amino]-4-oxo-2-butenoate

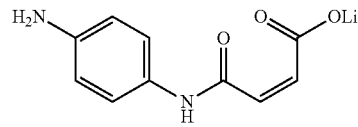

Under a nitrogen atmosphere, into a reaction vessel were charged 13.23 g (122.4 mmol) of 1,4-phenylenediamine and 225 ml of tetrahydrofuran. A solution prepared by dissolving 8.00 g (81.6 mmol) of maleic anhydride in 24 ml of tetrahydrofuran was dropped into this under cooling with ice over a period of 2 hours, then, the mixture was stirred at room temperature for 3 hours. After completion of the reaction, a solution prepared by dissolving 1.99 g (81.6 mmol) of 98% lithium hydroxide in 17.95 g of water was dropped at room temperature over a period of 30 minutes, and the mixture was stirred at room temperature for 1 hour. Thereafter, the solvent was distilled off under reduced pressure to obtain a residue to which 200 ml of 2-propanol was added, and the mixture was stirred at room temperature overnight. Thereafter, the deposited solid was isolated by filtration, and washed with 50 ml of 2-propanol. The resultant solid was dried under reduced pressure at 45° C. for 5 hours, to obtain 13.03 g of lithium (2Z)-4-[(4-aminophenyl)amino]-4-oxo-2-butenoate as a pate brown-white solid. Yield: 75.3%

$H^1$-NMR (270 MHz, DMSO-d6) $\delta_{p\,p\,m}$: 14.6 (1H, s), 7.3 (2H, d, J=8.9 Hz), 6.5 (2H, d, J=8.9 Hz), 6.1 (1H, d, J=13.5 Hz), 5.6 (1H, d, J=13.5 Hz), 4.8 (2H, s).

Example 7

Production of ammonium (2Z)-4-[(4-aminophenyl)amino]-4-oxo-2-butenoate mono-hydrate

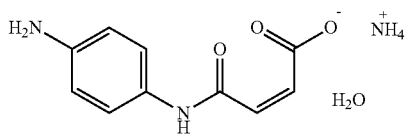

Under a nitrogen atmosphere, into a reaction vessel were charged 12.1 g (58.7 mmol) of (2Z)-4-[(4-aminophenyl)amino]-4-oxo-2-butenoic acid and 50 ml of water. A solution prepared by dissolving 12 ml of 25% ammonia water in 12 ml of water was dropped into this under cooling with ice over a period of 15 minutes. After completion of dropping, the solvent was distilled off under reduced pressure to obtain a residue to which 100 ml of tetrahydrofuran was added, and the mixture was stirred at 50° C. for 1 hour. Thereafter, the mixture was cooled down to room temperature, the deposited solid was isolated by filtration, and washed three times with 20 ml of tetrahydrofuran. The resultant solid was dried to obtain 11.1 g of ammonium (2Z)-4-[(4-aminophenyl)amino]-4-oxo-2-butenoate mono-hydrate as a gray-green powder. Yield: 79%.

$H^1$-NMR (300 MHz, DMSO-d6) $\delta_{ppm}$: 7.3 (2H, d, J=8.7 Hz), 6.5 (2H, d, J=8.7 Hz), 6.1 (1H, d, J=13.2 Hz), 5.9 (1H, d, J=13.2 Hz).

Example 8

Production of methyl (2Z)-4-[(4-aminophenyl)amino]-4-oxo-2-butenoate hydrochloride

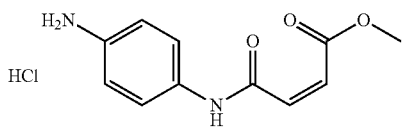 [SMILES: Cl ; COC(=O)/C=C\C(=O)Nc1ccc(N)cc1]

Under a nitrogen atmosphere, into a reaction vessel were charged 97.33 g (9000 mmol) of 1,4-phenylenediamine, 900 ml of tetrahydrofuran and 300 ml of dimethylformamide. A solution prepared by dissolving 45.6 g (3300 mmol) of potassium carbonate in 150 ml of water and a solution prepared by dissolving di-tert-butyl dicarbonate in 120 ml of tetrahydrofuran were dropped into this over a period of about 2 hours, and these were reacted at room temperature for 4 hours. After completion of the reaction, the reaction solution was discharged into 1200 ml of cold water, and extracted with 1000 ml of chloroform twice. The organic layers were combined, and washed with 750 ml of water and 750 ml of saturated saline, the organic layer was dried over anhydrous sodium sulfate and filtrated, and then, the solvent was distilled off, to obtain coarse tert-butyl-4-aminophenyl carbamate. Coarse tert-butyl-4-aminophenyl carbamate was purified by silica gel chromatography (developing solvent: methanol/chloroform=1/15), to obtain 56.9 g of tert-butyl-4-aminophenyl carbamate as a yellow-brown solid. Yield: 91%.

Under a nitrogen atmosphere, into a reaction vessel were charged 20 g (96.0 mmol) of tert-butyl-4-aminophenyl carbamate and 400 ml of tetrahydrofuran, a solution prepared by dissolving 9.4 q (96.0 mmol) of maleic anhydride in 28 ml of tetrahydrofuran was dropped under cooling with ice over a period of 25 minutes, then, the mixture was stirred at room temperature overnight. After completion of the reaction, the reaction solution was condensed under reduced pressure, to obtain 28.1 g of (2Z)-4-[(4-tert-butoxycarbonylaminophenyl)amino]-4-oxo-2-b utenoic acid as a yellow solid. Yield: 95.6%.

Under a nitrogen atmosphere, into a reaction vessel was charged 100 ml of methanol, and this was cooled to −10° C. Into this, 5.8 g (49.0 mmol) of thionyl chloride was dropped over a period of 10 minutes, and the mixture was stirred at −10° C. for 5 minutes. A solution prepared by dissolving 10.0 g (32.6 mmol) of (2Z)-4-[(4-tert-butoxycarbonylaminophenyl)amino]-4-oxo-2-b utenoic acid in 100 ml of methanol was dropped over a period of 20 minutes, then, the mixture was stirred at room temperature for 4 hours. The reaction solution was condensed under reduced pressure, to obtain coarse methyl (2Z)-4-[(4-aminophenyl)amino]-4-oxo-2-butenoate hydrochloride. To coarse methyl (2Z)-4-[(4-aminophenyl)amino]-4-oxo-2-butenoate hydrochloride was added 110 ml of a 10% methanol-chloroform solution, and the mixture was stirred at room temperature overnight, then, the deposited solid was isolated by filtration, and dried to obtain 6.8 g of methyl (2Z)-4-[(4-aminophenyl)amino]-4-oxo-2-butenoate hydrochloride as a pale brown-white solid. Yield: 94.7%.

$H^1$-NMR (300 MHz, DMSO-d6) $\delta_{ppm}$: 10.7 (1H, s), 7.7 (2H, d, J=8.7 Hz), 7.4 (2H, d, J=8.7 Hz), 6.6 (1H, d, J=11.7 Hz), 6.4 (1H, d, J=12.0 Hz), 3.67 (3H, s).

Example 9

Production of barium bis{(2Z)-4-[(4-aminophenyl)amino]-4-oxo-2-butenoate}di-hydrate

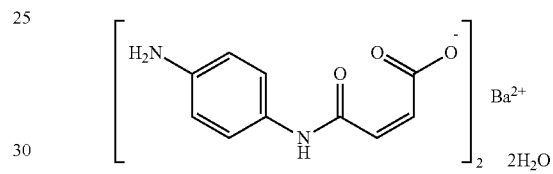

Under a nitrogen atmosphere, into a reaction vessel were charged 10.0 g (44.6 mmol) of (2Z)-4-[(4-aminophenyl)amino]-4-oxo-2-butenoic acid mono-hydrate obtained by the same method as in Production Example 2 and 70 ml of water, a solution prepared by dissolving 7.04 g (22.3 mmol) of barium hydroxide octa-hydrate in 30 ml of water was added at 20 to 30° C., and the mixture was stirred at room temperature for 2 hours. Thereafter, the mixture was condensed under reduced pressure and the solvent was distilled off to obtain a residue to which 50 ml of ethanol and 50 ml of 2-propanol were added, and the mixture was stirred at room temperature overnight, the deposited crystal was isolated by filtration, and dried under reduced pressure at 45° C., to obtain 12.4 g of barium bis{(2Z)-4-[(4-aminophenyl)amino]-4-oxo-2-butenoate}di-hydrate as a yellow solid. Yield: 98.3%.

$H^1$-NMR (270 MHz, DMSO-d6) $\delta_{ppm}$: 14.1 (2H, s), 7.3 (4H, d, J=8.6 Hz), 6.5 (4H, d, J=8.9 Hz), 6.1 (2H, d, J=13.5 Hz), 5.7 (2H, d, J=13.2 Hz), 4.8 (4H, s), 3.4 (4H, s).

Example 10

Production of Rubber Composition

<Procedure 1>

Using a Banbury mixer (manufactured by Toyo Seiki Seisakusho Co., Ltd., 600 ml Laboplastomill), 100 parts by weight of natural rubber (RSS#1), 45 parts by weight of HAF (manufactured by Asahi Carbon Co., Ltd., trade name "Asahi #70"), 3 parts by weight of stearic acid, 5 parts by weight of zinc oxide, 1 part by weight of an antioxidant (N-phenyl-N'-1,3-dimethylbutyl-p-phenylenediamine: trade name "Antigen (registered trademark) 6C", manufactured by Sumitomo Chemical Co., Ltd.) and 1 part by weight of (2Z)-4-[(4-aminophenyl)amino]-4-oxo-2-butenoic acid obtained in the above-described Production Example 1 were blended by kneading, to obtain a rubber composition. This procedure 1 was performed by charging various components, then, kneading them at a mixer rotating speed of 50 rpm for 5 minutes, and the rubber temperature in this operation was 160 to 170° C.

<Procedure 2>

In an open roll mill, the rubber composition obtained by the procedure 1, 1 part by weight of a vulcanization accelerator (N-cyclohexyl-2-benzothiazolyl sulfenamide) and 2 parts by weight of sulfur were blended by kneading at a temperature of 60 to 80° C., to obtain a rubber composition.

Example 11

Production of Vulcanized Rubber

The rubber composition obtained in the procedure 2 of Example 10 was vulcanization-treated at 145° C., to obtain vulcanized rubber.

Example 12

Production of Rubber Composition

A rubber composition was obtained in the same manner as in Example 10 excepting that (2Z)-4-[(4-aminophenyl)amino]-4-oxo-2-butenoic acid mono-hydrate obtained in the above-described Production Example 2 was used instead of (2Z)-4-[(4-aminophenyl)amino]-4-oxo-2-butenoic acid in Example 10.

Example 13

Production of Vulcanized Rubber

The rubber composition obtained in the procedure 2 of Example 12 was vulcanization-treated at 145° C., to obtain vulcanized rubber.

Example 14

Production of Rubber Composition

A rubber composition was obtained in the same manner as in Example 10 excepting that (2Z)-4-[(3-aminophenyl)amino]-4-oxo-2-butenoic acid obtained in the above-described Production Example 3 was used instead of (2Z)-4-[(4-aminophenyl)amino]-4-oxo-2-butenoic acid in Example 10.

Example 15

Production of Vulcanized Rubber

The rubber composition obtained in the procedure 2 of Example 14 was vulcanization-treated at 145° C., to obtain vulcanized rubber.

Example 16

Production of Rubber Composition

A rubber composition was obtained in the same manner as in Example 10 excepting that (2Z)-4-[(4-aminophenyl)amino]-2-methyl4-oxo-2-butenoic acid obtained in the above-described Production Example 4 was used instead of (2Z)-4-[(4-aminophenyl)amino]-4-oxo-2-butenoic acid in Example 10.

Example 17

Production of Vulcanized Rubber

The rubber composition obtained in the procedure 2 of Example 16 was vulcanization-treated at 145° C., to obtain vulcanized rubber.

Example 18

Production of Rubber Composition

A rubber composition was obtained in the same manner as in Example 10 excepting that (2Z)-4-[(6-aminohexyl)amino]-4-oxo-2-butenoic acid obtained in the above-described Production Example 5 was used instead of (2Z)-4-[(4-aminophenyl)amino]-4-oxo-2-butenoic acid in Example 10.

Example 19

Production of Vulcanized Rubber

The rubber composition obtained in the procedure 2 of Example 18 was vulcanization-treated at 145° C., to obtain vulcanized rubber.

Example 20

Production of Rubber Composition

A rubber composition was obtained in the same manner as in Example 10 excepting that (2Z)-4-[(4-aminophenyl)amino]-4-oxo-2-butenoic acid methanol solvate obtained in the above-described Example 1 was used instead of (2Z)-4-[(4-aminophenyl)amino]-4-oxo-2-butenoic acid in Example 10.

Example 21

Production of Vulcanized Rubber

The rubber composition obtained in the procedure 2 of Example 20 was vulcanization-treated at 145° C., to obtain vulcanized rubber.

Example 22

Production of Rubber Composition

A rubber composition was obtained in the same manner as in Example 10 excepting that sodium (2Z)-4-[(4-aminophenyl)amino]-4-oxo-2-butenoate obtained in the above-described Example 2 was used instead of (2Z)-4-[(4-aminophenyl)amino]-4-oxo-2-butenoic acid in Example 10.

Example 23

Production of Vulcanized Rubber

The rubber composition obtained in the procedure 2 of Example 22 was vulcanization-treated at 145° C., to obtain vulcanized rubber.

Example 24

Production of Rubber Composition

A rubber composition was obtained in the same manner as in Example 10 excepting that sodium (2Z)-4-[(4-aminophenyl)amino]-4-oxo-2-butenoate di-hydrate obtained in the above-described Example 3 was used instead of (2Z)-4-[(4-aminophenyl)amino]-4-oxo-2-butenoic acid in Example 10.

Example 25

Production of Vulcanized Rubber

The rubber composition obtained in the procedure 2 of Example 24 was vulcanization-treated at 145° C., to obtain vulcanized rubber.

Example 26

Production of Rubber Composition

A rubber composition was obtained in the same manner as in Example 10 excepting that sodium (2Z)-4-[(4-aminophenyl)amino]-4-oxo-2-butenoate methanol solvate obtained in the above-described Example 4 was used instead of (2Z)-4-[(4-aminophenyl)amino]-4-oxo-2-butenoic acid in Example 10.

Example 27

Production of Vulcanized Rubber

The rubber composition obtained in the procedure 2 of Example 26 was vulcanization-treated at 145° C., to obtain vulcanized rubber.

Example 28

Production of Rubber Composition

A rubber composition was obtained in the same manner as in Example 10 excepting that potassium (2Z)-4-[(4-aminophenyl)amino]-4-oxo-2-butenoate mono-hydrate obtained in the above-described Example 5 was used instead of (2Z)-4-[(4-aminophenyl)amino]-4-oxo-2-butenoic acid in Example 10.

Example 29

Production of Vulcanized Rubber

The rubber composition obtained in the procedure 2 of Example 28 was vulcanization-treated at 145° C., to obtain vulcanized rubber.

Example 30

Production of Rubber Composition

A rubber composition was obtained in the same manner as in Example 10 excepting that lithium (2Z)-4-[(4-aminophenyl)amino]-4-oxo-2-butenoate obtained in the above-described Example 6 was used instead of (2Z)-4-[(4-aminophenyl)amino]-4-oxo-2-butenoic acid in Example 10.

Example 31

Production of Vulcanized Rubber

The rubber composition obtained in the procedure 2 of Example 30 was vulcanization-treated at 145° C., to obtain vulcanized rubber.

Example 32

Production of Rubber Composition

A rubber composition was obtained in the same manner as in Example 10 excepting that ammonium (2Z)-4-[(4-aminophenyl)amino]-4-oxo-2-butenoate mono-hydrate obtained in the above-described Example 7 was used instead of (2Z)-4-[(4-aminophenyl)amino]-4-oxo-2-butenoic acid in Example 10.

Example 33

Production of Vulcanized Rubber

The rubber composition obtained in the procedure 2 of Example 32 was vulcanization-treated at 145° C., to obtain vulcanized rubber.

Example 34

Production of Rubber Composition

A rubber composition was obtained in the same manner as in Example 10 excepting that methyl (2Z)-4-[(4-aminophenyl)amino]-4-oxo-2-butenoate hydrochloride obtained in the above-described Example 8 was used instead of (2Z)-4-[(4-aminophenyl)amino]-4-oxo-2-butenoic acid in Example 10.

Example 35

Production of Vulcanized Rubber

The rubber composition obtained in the procedure 2 of Example 34 was vulcanization-treated at 145° C., to obtain vulcanized rubber.

Example 36

Production of Rubber Composition

A rubber composition was obtained in the same manner as in Example 10 excepting that barium bis{(2Z)-4-[(4-aminophenyl)amino]-4-oxo-2-butenoate}di-hydrate obtained in the above-described Example 9 was used instead of (2Z)-4-[(4-aminophenyl)amino]-4-oxo-2-butenoic acid in Example 10.

Example 37

Production of Vulcanized Rubber

The rubber composition obtained in the procedure 2 of Example 36 was vulcanization-treated at 145° C., to obtain vulcanized rubber.

Reference Example 1

A rubber composition was obtained in the same manner as in Example 10 excepting that (2Z)-4-[(4-aminophenyl)amino]-4-oxo-2-butenoic acid was not used in Example 10.

Reference Example 2

The rubber composition obtained in the procedure 2 of Reference Example 1 was vulcanization-treated at 145° C., to obtain vulcanized rubber.

The scorch time and the viscoelastic property were measured as described below.

(1) Scorch Time

The scorch time was measured at 125° C. according to JIS-K6300-1.

The larger value of the scorch time denotes a lower possibility of rubber burning and better processing stability.

The relative values of the scorch times of the rubber compositions obtained in Examples 10, 12, 14, 16, 18, 20, 22, 24, 26, 28, 30, 32, 34 and 36 were denoted by index numbers with respect to 100 of the scorch time of the rubber composition obtained in Reference Example 1, using the rubber composition obtained in Reference Example 1 as a control. The results are shown in Table 1.

TABLE 1

|  | scorch time |
| --- | --- |
| Example 10 | 97 |
| Example 12 | 97 |
| Example 14 | 117 |
| Example 16 | 88 |
| Example 18 | 77 |
| Example 20 | 90 |
| Example 22 | 86 |
| Example 24 | 96 |
| Example 26 | 85 |
| Example 28 | 78 |
| Example 30 | 82 |
| Example 32 | 96 |
| Example 34 | 113 |
| Example 36 | 88 |

(2) Viscoelastic Property

The viscoelastic property was measured using Viscoelasticity Analyzer manufactured by Ueshima Seisakusho Co., Ltd.

Condition; temperature: −5° C. to 80° C. (temperature rising rate: 2° C./min), initial strain: 10%, dynamic strain: 2.5%, frequency: 10 Hz The decreasing rate (%) in the viscoelastic property (tan δ at 60° C.) of the vulcanized rubber obtained in Examples 11, 13, 15, 17, 19, 21, 23, 25, 27, 29, 31, 33, 35 and 37 with respect to the vulcanized rubber obtained in Reference Example 2 was measured, using the vulcanized rubber obtained in Reference Example 2 as a control. The results are shown in Table 2.

TABLE 2

|  | The decreasing rate (%) |
| --- | --- |
| Example 11 | 25 |
| Example 13 | 26 |
| Example 15 | 17 |
| Example 17 | 13 |
| Example 19 | 18 |
| Example 21 | 25 |
| Example 23 | 23 |
| Example 25 | 25 |
| Example 27 | 26 |
| Example 29 | 19 |
| Example 31 | 20 |
| Example 33 | 22 |
| Example 35 | 25 |
| Example 37 | 23 |

Example 38

Production of Rubber Composition

<Procedure 1>

Using a Banbury mixer (manufactured by Toyo Seiki Seisakusho Co., Ltd., 600 ml Laboplastomill), 100 parts by weight of natural rubber (RSS#1), 45 parts by weight of HAF (manufactured by Asahi Carbon Co., Ltd., trade name "Asahi #70"), 3 parts by weight of stearic acid, 5 parts by weight of zinc oxide, 1 part by weight of an antioxidant (N-phenyl-N'-1,3-dimethylbutyl-p-phenylenediamine: trade name "Antigen (registered trademark) 6C", manufactured by Sumitomo Chemical Co., Ltd.) and 0.5 parts by weight of (2Z)-4-[(4-aminophenyl)amino]-4-oxo-2-butenoic acid obtained in the above-described Production Example 1 were blended by kneading, to obtain a rubber composition. This procedure 1 was performed by charging various components, then, kneading them at a mixer rotating speed of 50 rpm for 5 minutes, and the rubber temperature in this operation was 160 to 170° C.

<Procedure 2>

In an open roll mill, the rubber composition obtained by the procedure 1, 1 part by weight of a vulcanization accelerator (N-cyclohexyl-2-benzothiazolyl sulfenamide) and 2 parts by weight of sulfur were blended by kneading at a temperature of 60 to 80° C., to obtain a rubber composition.

Example 39

Production of Vulcanized Rubber

The rubber composition obtained in the procedure 2 of Example 38 was vulcanization-treated at 145° C., to obtain vulcanized rubber.

Example 40

Production of Rubber Composition

A rubber composition was obtained in the same manner as in Example 38 excepting that 1 part by weight of (2Z)-4-[(4-aminophenyl)amino]-4-oxo-2-butenoic acid was used in Example 38.

Example 41

Production of Vulcanized Rubber

The rubber composition obtained in the procedure 2 of Example 40 was vulcanization-treated at 145° C., to obtain vulcanized rubber.

Example 42

Production of Rubber Composition

A rubber composition was obtained in the same manner as in Example 38 excepting that 2 parts by weight of (2Z)-4-[(4-aminophenyl)amino]-4-oxo-2-butenoic acid was used in Example 38.

Example 43

Production of Vulcanized Rubber

The rubber composition obtained in the procedure 2 of Example 42 was vulcanization-treated at 145° C., to obtain vulcanized rubber.

Reference Example 3

A rubber composition was obtained in the same manner as in Example 38 excepting that (2Z)-4-[(4-aminophenyl)amino]-4-oxo-2-butenoic acid was not used in Example 38.

Reference Example 4

The rubber composition obtained in the procedure 2 of Reference Example 3 was vulcanization-treated at 145° C., to obtain vulcanized rubber.

The scorch time and the viscoelastic property were measured as described below.

(1) Scorch Time

The scorch time was measured at 125° C. according to JIS-K6300-1.

The larger value of the scorch time denotes a lower possibility of rubber burning and better processing stability.

The relative values of the scorch times of the rubber compositions obtained in Examples 38, 40 and 42 were denoted by index numbers with respect to 100 of the scorch time of the rubber composition obtained in Reference Example 3, using the rubber composition obtained in Reference Example 3 as a control.

The results are shown in Table 3.

TABLE 3

|  | scorch time |
|---|---|
| Example 38 | 94 |
| Example 40 | 89 |
| Example 42 | 81 |

(2) Viscoelastic Property

The viscoelastic property was measured using Viscoelasticity Analyzer manufactured by Ueshima Seisakusho Co., Ltd.

Condition; temperature: −5° C. to 80° C. (temperature rising rate: 2° C./min), initial strain: 10%, dynamic strain: 2.5%, frequency: 10 Hz The decreasing rate (%) in the viscoelastic property (tan δ at 60° C.) of the vulcanized rubber obtained in Examples 39, 41 and 43 with respect to the vulcanized rubber obtained in Reference Example 4 was measured, using the vulcanized rubber obtained in Reference Example 4 as a control. The results are shown in Table 4.

TABLE 4

|  | The decreasing rate (%) |
|---|---|
| Example 39 | 18 |
| Example 41 | 24 |
| Example 43 | 27 |

Example 44

Production of Rubber Composition

<Procedure 1>

Using a Banbury mixer (manufactured by Toyo Seiki Seisakusho Co., Ltd., 600 ml Laboplastomill), 100 parts by weight of natural rubber (RSS#1), 45 parts by weight of HAF (manufactured by Asahi Carbon Co., Ltd., trade name "Asahi #70"), 3 parts by weight of stearic acid, 5 parts by weight of zinc oxide, 1 part by weight of an antioxidant (N-phenyl-N'-1,3-dimethylbutyl-p-phenylenediamine: trade name "Antigen (registered trademark) 6C", manufactured by Sumitomo Chemical Co., Ltd.) and 0.5 parts by weight of sodium (2Z)-4-[(4-aminophenyl)amino]-4-oxo-2-butenoate di-hydrate obtained in the above-described Example 3 were blended by kneading, to obtain a rubber composition. This procedure 1 was performed by charging various components, then, kneading them at a mixer rotating speed of 50 rpm for 5 minutes, and the rubber temperature in this operation was 160 to 170° C.

<Procedure 2>

In an open roll mill, the rubber composition obtained by the procedure 1, 1 part by weight of a vulcanization accelerator (N-cyclohexyl-2-benzothiazolyl sulfenamide) and 2 parts by weight of sulfur were blended by kneading at a temperature of 60 to 80° C., to obtain a rubber composition.

Example 45

Production of Vulcanized Rubber

The rubber composition obtained in the procedure 2 of Example 44 was vulcanization-treated at 145° C., to obtain vulcanized rubber.

Example 46

Production of Rubber Composition

A rubber composition was obtained in the same manner as in Example 44 excepting that 1 part by weight of sodium (2Z)-4-[(4-aminophenyl)amino]-4-oxo-2-butenoate di-hydrate was used in Example 44.

Example 47

Production of Vulcanized Rubber

The rubber composition obtained in the procedure 2 of Example 46 was vulcanization-treated at 145° C., to obtain vulcanized rubber.

Example 48

Production of Rubber Composition

A rubber composition was obtained in the same manner as in Example 44 excepting that 2 parts by weight of sodium (2Z)-4-[(4-aminophenyl)amino]-4-oxo-2-butenoate di-hydrate was used in Example 44.

Example 49

Production of Vulcanized Rubber

The rubber composition obtained in the procedure 2 of Example 48 was vulcanization-treated at 145° C., to obtain vulcanized rubber.

Reference Example 5

A rubber composition was obtained in the same manner as in Example 44 excepting that sodium (2Z)-4-[(4-aminophenyl)amino]-4-oxo-2-butenoate di-hydrate was not used in Example 44.

Reference Example 6

The rubber composition obtained in the procedure 2 of Reference Example 5 was vulcanization-treated at 145° C., to obtain vulcanized rubber.

The scorch time and the viscoelastic property were measured as described below.
(1) Scorch Time The scorch time was measured at 125° C. according to JIS-K6300-1.

The larger value of the scorch time denotes a lower possibility of rubber burning and better processing stability.

The relative values of the scorch times of the rubber compositions obtained in Examples 44, 46 and 48 were denoted by index numbers with respect to 100 of the scorch time of the rubber composition obtained in Reference Example 5, using the rubber composition obtained in Reference Example 5 as a control. The results are shown in Table 5.

TABLE 5

|  | scorch time |
| --- | --- |
| Example 44 | 85 |
| Example 46 | 78 |
| Example 48 | 65 |

(2) Viscoelastic Property

The viscoelastic property was measured using Viscoelasticity Analyzer manufactured by Ueshima Seisakusho Co., Ltd.

Condition; temperature: −5° C. to 80° C. (temperature rising rate: 2° C./min), initial strain: 10%, dynamic strain: 2.5%, frequency: 10 Hz The decreasing rate (%) in the viscoelastic property (tan δ at 60° C.) of the vulcanized rubber obtained in Examples 45, 47 and 49 with respect to the vulcanized rubber obtained in Reference Example 6 was measured, using the vulcanized rubber obtained in Reference Example 6 as a control. The results are shown in Table 6.

TABLE 6

|  | The decreasing rate (%) |
| --- | --- |
| Example 45 | 21 |
| Example 47 | 28 |
| Example 49 | 33 |

Example 50

Production of Rubber Composition

<Procedure 1>

Using a Banbury mixer (manufactured by Toyo Seiki Seisakusho Co., Ltd., 600 ml Laboplastomill), 100 parts by weight of natural rubber (RSS#1), 45 parts by weight of ISAF (manufactured by Asahi Carbon Co., Ltd., trade name "Asahi #80"), 3 parts by weight of stearic acid, 5 parts by weight of zinc oxide, 1 part by weight of an antioxidant (N-phenyl-N'-1,3-dimethylbutyl-p-phenylenediamine: trade name "Antigen (registered trademark) 6C", manufactured by Sumitomo Chemical Co., Ltd.) and 0.57 parts by weight of (2Z)-4-[(4-aminophenyl)amino]-4-oxo-2-butenoic acid obtained in the above-described Production Example 1 were blended by kneading, to obtain a rubber composition. This procedure 1 was performed by charging various components, then, kneading them at a mixer rotating speed of 50 rpm for 5 minutes, and the rubber temperature in this operation was 160 to 170° C.
<Procedure 2>

In an open roll mill, the rubber composition obtained by the procedure 1, 1 part by weight of a vulcanization accelerator (N-cyclohexyl-2-benzothiazolyl sulfenamide) and 2 parts by weight of sulfur were blended by kneading at a temperature of 60 to 80° C., to obtain a rubber composition.

Example 51

Production of Vulcanized Rubber

The rubber composition obtained in the procedure 2 of Example 50 was vulcanization-treated at 145° C., to obtain vulcanized rubber.

Reference Example 7

A rubber composition was obtained in the same manner as in Example 50 excepting that (2Z)-4-[(4-aminophenyl)amino]-4-oxo-2-butenoic acid was not used in Example 50.

Reference Example 8

The rubber composition obtained in the procedure 2 of Reference Example 7 was vulcanization-treated at 145° C., to obtain vulcanized rubber.

Example 52

Production of Rubber Composition

A rubber composition was obtained in the same manner as in Example 50 excepting that HAF-LS (manufactured by Asahi Carbon Co., Ltd., trade name "Asahi #70L") was used instead of ISAF (manufactured by Asahi Carbon Co., Ltd., trade name "Asahi #80") in Example 50.

Example 53

Production of Vulcanized Rubber

The rubber composition obtained in the procedure 2 of Example 52 was vulcanization-treated at 145° C., to obtain vulcanized rubber.

Reference Example 9

A rubber composition was obtained in the same manner as in Example 52 excepting that (2Z)-4-[(4-aminophenyl) amino]-4-oxo-2-butenoic acid was not Used in Example 52.

Reference Example 10

The rubber composition obtained in the procedure 2 of Reference Example 9 was vulcanization-treated at 145° C., to obtain vulcanized rubber.

Example 54

Production of Rubber Composition

A rubber composition was obtained in the same manner as in Example 50 excepting that HAF (manufactured by Asahi Carbon Co., Ltd., trade name "Asahi #70") was used instead of ISAF (manufactured by Asahi Carbon Co., Ltd., trade name "Asahi #80") in Example 50.

Example 55

Production of Vulcanized Rubber

The rubber composition obtained in the procedure 2 of Example 54 was vulcanization-treated at 145° C., to obtain vulcanized rubber.

Reference Example 11

A rubber composition was obtained in the same manner as in Example 54 excepting that (2Z)-4-[(4-aminophenyl) amino]-4-oxo-2-butenoic acid was not used in Example 54.

Reference Example 12

The rubber composition obtained in the procedure 2 of Reference Example 11 was vulcanization-treated at 145° C., to obtain vulcanized rubber.

Example 56

Production of Rubber Composition

A rubber composition was obtained in the same manner as in Example 50 excepting that FEF (manufactured by Asahi Carbon Co., Ltd., trade name "Asahi #60") was used instead of ISAF (manufactured by Asahi Carbon Co., Ltd., trade name "Asahi #80") in Example 50.

Example 57

Production of Vulcanized Rubber

The rubber composition obtained in the procedure 2 of Example 56 was vulcanization-treated at 145° C., to obtain vulcanized rubber.

Reference Example 13

A rubber composition was obtained in the same manner as in Example 56 excepting that (2Z)-4-[(4-aminophenyl) amino]-4-oxo-2-butenoic acid was not used in Example 56.

Reference Example 14

The rubber composition obtained in the procedure 2 of Reference Example 13 was vulcanization-treated at 145° C., to obtain vulcanized rubber.

Example 58

Production of Rubber Composition

A rubber composition was obtained in the same manner as in Example 50 excepting that GPF (manufactured by Asahi Carbon Co., Ltd., trade name "Asahi #55") was used instead of ISAF (manufactured by Asahi Carbon Co., Ltd., trade name "Asahi #80") in Example 50.

Example 59

Production of Vulcanized Rubber

The rubber composition obtained in the procedure 2 of Example 58 was vulcanization-treated at 145° C., to obtain vulcanized rubber.

Reference Example 15

A rubber composition was obtained in the same manner as in Example 58 excepting that (2Z)-4-[(4-aminophenyl) amino]-4-oxo-2-butenoic acid was not used in Example 58.

Reference Example 16

The rubber composition obtained in the procedure 2 of Reference Example 15 was vulcanization-treated at 145° C., to obtain vulcanized rubber.

The scorch time and the viscoelastic property were measured as described below.

(1) Scorch Time

The scorch time was measured at 125° C. according to JIS-K6300-1.

The larger value of the scorch time denotes a lower possibility of rubber burning and better processing stability.

The relative values of the scorch times of the rubber compositions obtained in Examples 50, 52, 54, 56 and 58 were denoted by index numbers with respect to 100 of the scorch time of the rubber composition obtained in Reference Examples 7, 9, 11, 13 and 15, using the rubber composition obtained in Reference Examples 7, 9, 11, 13 and 15 as a control. The results are shown in Table 7.

TABLE 7

|  | Control Reference Example | scorch time |
|---|---|---|
| Example 50 | Reference Example 7 | 95 |
| Example 52 | Reference Example 9 | 100 |
| Example 54 | Reference Example 11 | 99 |
| Example 56 | Reference Example 13 | 96 |
| Example 58 | Reference Example 15 | 99 |

(2) Viscoelastic Property

The viscoelastic property was measured using Viscoelasticity Analyzer manufactured by Ueshima Seisakusho Co., Ltd.

Condition; temperature: −5° C. to 80° C. (temperature rising rate: 2° C./min), initial strain: 10%, dynamic strain: 2.5%, frequency: 10 Hz The decreasing rate (%) in the viscoelasting property (tan δ at 60° C.) of the vulcanized rubber obtained in Examples 51, 53, 55, 57 and 59 with respect to the vulcanized rubber obtained in Reference Examples 8, 10, 12, 14 and 16 was measured, using the vulcanized rubber obtained in Reference Examples 8, 10, 12, 14 and 16 as a control. The results are shown in Table 8.

TABLE 8

|  | Control Reference Example | The decreasing rate (%) |
|---|---|---|
| Example 51 | Reference Example 8 | 9 |
| Example 53 | Reference Example 10 | 18 |
| Example 55 | Reference Example 12 | 11 |
| Example 57 | Reference Example 14 | 23 |
| Example 59 | Reference Example 16 | 34 |

Example 60

Production of Rubber Composition

<Procedure 1>

Using a Banbury mixer (manufactured by Toyo Seiki Seisakusho Co., Ltd., 600 ml Laboplastomill), 100 parts by weight of natural rubber (RSS#1), 45 parts by weight of ISAF (manufactured by Asahi Carbon Co., Ltd., trade name "Asahi #80"), 3 parts by weight of stearic acid, 5 parts by weight of zinc oxide, 1 part by weight of an antioxidant (N-phenyl-N'-1,3-dimethylbutyl-p-phenylenediamine: trade name "Antigen (registered trademark) 6C", manufactured by Sumitomo Chemical Co., Ltd.) and 1 part by weight of sodium (2Z)-4-[(4-aminophenyl)amino]-4-oxo-2-butenoate methanol solvate obtained in the above-described Example 4 were blended by kneading, to obtain a rubber composition. This procedure 1 was performed by charging various components, then, kneading them at a mixer rotating speed of 50 rpm for 5 minutes, and the rubber temperature in this operation was 160 to 170° C.

<Procedure 2>

In an open roll mill, the rubber composition obtained by the procedure 1, 1 part by weight of a vulcanization accelerator (N-cyclohexyl-2-benzothiazolyl sulfenamide) and 2 parts by weight of sulfur were blended by kneading at a temperature of 60 to 80° C., to obtain a rubber composition.

Example 61

Production of Vulcanized Rubber

The rubber composition obtained in the procedure 2 of Example 60 was vulcanization-treated at 145° C., to obtain vulcanized rubber.

Reference Example 17

A rubber composition was obtained in the same manner as in Example 60 excepting that sodium (2Z)-4-[(4-aminophenyl)amino]-4-oxo-2-butenoate methanol solvate was not used in Example 60.

Reference Example 18

The rubber composition obtained in the procedure 2 of Reference Example 17 was vulcanization-treated at 145° C., to obtain vulcanized rubber.

Example 62

Production of Rubber Composition

A rubber composition was obtained in the same manner as in Example 60 excepting that HAF-LS (manufactured by Asahi Carbon Co., Ltd., trade name "Asahi #70L") was used instead of ISAF (manufactured by Asahi Carbon Co., Ltd., trade name "Asahi #80") in Example 60.

Example 63

Production of Vulcanized Rubber

The rubber composition obtained in the procedure 2 of Example 62 was vulcanization-treated at 145° C., to obtain vulcanized rubber.

Reference Example 19

A rubber composition was obtained in the same manner as in Example 62 excepting that sodium (2Z)-4-[(4-aminophenyl)amino]-4-oxo-2-butenoate methanol solvate was not used in Example 62.

Reference Example 20

The rubber composition obtained in the procedure 2 of Reference Example 19 was vulcanization-treated at 145° C., to obtain vulcanized rubber.

Example 64

Production of Rubber Composition

A rubber composition was obtained in the same manner as in Example 60 excepting that HAF (manufactured by Asahi Carbon Co., Ltd., trade name "Asahi #70") was used instead of ISAF (manufactured by Asahi Carbon Co., Ltd., trade name "Asahi #80") in Example 60.

Example 65

Production of Vulcanized Rubber

The rubber composition obtained in the procedure 2 of Example 64 was vulcanization-treated at 145° C., to obtain vulcanized rubber.

Reference Example 21

A rubber composition was obtained in the same manner as in Example 64 excepting that sodium (2Z)-4-[(4-aminophenyl)amino]-4-oxo-2-butenoate methanol solvate was not used in Example 64.

Reference Example 22

The rubber composition obtained in the procedure 2 of Reference Example 21 was vulcanization-treated at 145° C., to obtain vulcanized rubber.

Example 66

Production of Rubber Composition

A rubber composition was obtained in the same manner as in Example 60 excepting that HAF-HS (manufactured by Showa Cabot Corp., trade name "ShoBlack N339") was used instead of ISAF (manufactured by Asahi Carbon Co., Ltd., trade name "Asahi #80") in Example 60.

Example 67

Production of Vulcanized Rubber

The rubber composition obtained in the procedure 2 of Example 66 was vulcanization-treated at 145° C., to obtain vulcanized rubber.

Reference Example 23

A rubber composition was obtained in the same manner as in Example 66 excepting that sodium (2Z)-4-[(4-aminophenyl)amino]-4-oxo-2-butenoate methanol solvate was not used in Example 66.

Reference Example 24

The rubber composition obtained in the procedure 2 of Reference Example 23 was vulcanization-treated at 145° C., to obtain vulcanized rubber.

Example 68

Production of Rubber Composition

A rubber composition was obtained in the same manner as in Example 60 excepting that FEF (manufactured by Asahi Carbon Co., Ltd., trade name "Asahi #60") was used instead of ISAF (manufactured by Asahi Carbon Co., Ltd., trade name "Asahi #80") in Example 60.

Example 69

Production of Vulcanized Rubber

The rubber composition obtained in the procedure 2 of Example 68 was vulcanization-treated at 145° C., to obtain vulcanized rubber.

Reference Example 25

A rubber composition was obtained in the same manner as in Example 68 excepting that sodium (2Z)-4-[(4-aminophenyl)amino]-4-oxo-2-butenoic acid methanol solvate was not used in Example 68.

Reference Example 26

The rubber composition obtained in the procedure 2 of Reference Example 25 was vulcanization-treated at 145° C., to obtain vulcanized rubber.

Example 70

Production of Rubber Composition

A rubber composition was obtained in the same manner as in Example 60 excepting that GPF (manufactured by Asahi Carbon Co., Ltd., trade name "Asahi #55") was used instead of ISAF (manufactured by Asahi Carbon Co., Ltd., trade name "Asahi #80") in Example 60.

Example 71

Production of Vulcanized Rubber

The rubber composition obtained in the procedure 2 of Example 70 was vulcanization-treated at 145° C., to obtain vulcanized rubber.

Reference Example 27

A rubber composition was obtained in the same manner as in Example 70 excepting that sodium (2Z)-4-[(4-aminophenyl)amino]-4-oxo-2-butenoate methanol solvate was not used in Example 70.

Reference Example 28

The rubber composition obtained in the procedure 2 of Reference Example 27 was vulcanization-treated at 145° C., to obtain vulcanized rubber.

The scorch time and the viscoelastic property were measured as described below.

(1) Scorch Time

The scorch time was measured at 125° C. according to JIS-K6300-1.

The larger value of the scorch time denotes a lower possibility of rubber burning and better processing stability.

The relative values of the scorch times of the rubber compositions obtained in Examples 60, 62, 64, 66, 68 and 70 were denoted by index numbers with respect to 100 of the scorch time of the rubber composition obtained in Reference Examples 17, 19, 21, 23, 25 and 27, using the rubber composition obtained in Reference Examples 17, 19, 21, 23, 25 and 27 as a control. The results are shown in Table 9.

TABLE 9

|  | Control Reference Example | scorch time |
| --- | --- | --- |
| Example 60 | Reference Example 17 | 88 |
| Example 62 | Reference Example 19 | 91 |
| Example 64 | Reference Example 21 | 87 |
| Example 66 | Reference Example 23 | 86 |
| Example 68 | Reference Example 25 | 85 |
| Example 70 | Reference Example 27 | 87 |

(2) Viscoelastic Property

The viscoelastic property was measured using Viscoelasticity Analyzer manufactured by Ueshima Seisakusho Co., Ltd.

Condition; temperature: −5° C. to 80° C. (temperature rising rate: 2° C./min), initial strain: 10%, dynamic strain: 2.5%, frequency: 10 Hz The decreasing rate (%) in the viscoelastic property (tan δ at 60° C.) of the vulcanized rubber obtained in Examples 61, 63, 65, 67, 69 and 71 with respect to the vulcanized rubber obtained in Reference Examples 18, 20, 22, 24, 26 and 28 was measured, using the vulcanized rubber obtained in Reference Examples 18, 20, 22, 24, 26 and 28 as a control. The results are shown in Table 10.

TABLE 10

|  | Control Reference Example | The decreasing rate (%) |
| --- | --- | --- |
| Example 61 | Reference Example 18 | 18 |
| Example 63 | Reference Example 20 | 25 |

TABLE 10-continued

|  | Control Reference Example | The decreasing rate (%) |
|---|---|---|
| Example 65 | Reference Example 22 | 31 |
| Example 67 | Reference Example 24 | 26 |
| Example 69 | Reference Example 26 | 44 |
| Example 71 | Reference Example 28 | 41 |

Example 72

Production of Rubber Composition

<Procedure 1>

Using a Banbury mixer (manufactured by Toyo Seiki Seisakusho Co., Ltd., 600 ml Laboplastomill), 100 parts by weight of natural rubber (RSS#1), 45 parts by weight of HAF (manufactured by Asahi Carbon Co., Ltd., trade name "Asahi #70"), 3 parts by weight of stearic acid, 5 parts by weight of zinc oxide, 1 part by weight of an antioxidant (N-phenyl-N'-1,3-dimethylbutyl-p-phenylenediamine: trade name "Antigen (registered trademark) 6C", manufactured by Sumitomo Chemical Co., Ltd.) and 0.57 parts by weight of (2Z)-4-[(4-aminophenyl)amino]-4-oxo-2-butenoic acid obtained in the above-described Production Example 1 were blended by kneading, to obtain a rubber composition. This procedure 1 was performed by charging various components, then, kneading them at a mixer rotating speed of 50 rpm for 5 minutes, and the rubber temperature in this operation was 160 to 170° C.

<Procedure 2>

In an open roll mill, the rubber composition obtained by the procedure 1, 1 part by weight of a vulcanization accelerator (N-cyclohexyl-2-benzothiazolyl sulfenamide) and 2 parts by weight of sulfur were blended by kneading at a temperature of 60 to 80° C., to obtain a rubber composition.

Example 73

Production of Vulcanized Rubber

The rubber composition obtained in the procedure 2 of Example 72 was vulcanization-treated at 145° C., to obtain vulcanized rubber.

Reference Example 29

A rubber composition was obtained in the same manner as in Example 72 excepting that (2Z)-4-[(4-aminophenyl)amino]-4-oxo-2-butenoic acid was not used in Example 72.

Reference Example 30

The rubber composition obtained in the procedure 2 of Reference Example 29 was vulcanization-treated at 145° C., to obtain vulcanized rubber.

Example 74

Production of Rubber Composition

A rubber composition was obtained in the same manner as in Example 72 excepting that 50 parts by weight of natural rubber (RSS#1) and 50 parts by weight of polybutadiene rubber (manufactured by JSR, "BR01") were used instead of 100 parts by weight of natural rubber (RSS#1) in Example 72.

Example 75

Production of Vulcanized Rubber

The rubber composition obtained in the procedure 2 of Example 74 was vulcanization-treated at 145° C., to obtain vulcanized rubber.

Reference Example 31

A rubber composition was obtained in the same manner as in Example 74 excepting that (2Z)-4-[(4-aminophenyl)amino]-4-oxo-2-butenoic acid was not used in Example 74.

Reference Example 32

The rubber composition obtained in the procedure 2 of Reference Example 31 was vulcanization-treated at 145° C., to obtain vulcanized rubber.

Example 76

Production of Rubber Composition

A rubber composition was obtained in the same manner as in Example 72 excepting that 60 parts by weight of natural rubber (RSS#1) and 40 parts by weight of styrene-butadiene copolymerized rubber SBR#1500 (manufactured by JSR) were used instead of 100 parts by weight of the natural rubber (RSS#1) in Example 72.

Example 77

Production of Vulcanized Rubber

The rubber composition obtained in the procedure 2 of Example 76 was vulcanization-treated at 145° C., to obtain vulcanized rubber.

Reference Example 33

A rubber composition was obtained in the same manner as in Example 76 excepting that (2Z)-4-[(4-aminophenyl)amino]-4-oxo-2-butenoic acid was not used in Example 76.

Reference Example 34

The rubber composition obtained in the procedure 2 of Reference Example 33 was vulcanization-treated at 145° C., to obtain vulcanized rubber.

The scorch time and the viscoelastic property were measured as described below.

(1) Scorch Time

The scorch time was measured at 125° C. according to JIS-K6300-1.

The larger value of the scorch time denotes a lower possibility of rubber burning and better processing stability.

The relative values of the scorch times of the rubber compositions obtained in Examples 72, 74 and 76 were denoted by index numbers with respect to 100 of the scorch time of the rubber composition obtained in Reference Examples 29, 31 and 33, using the rubber composition obtained in Reference Examples 29, 31 and 33 as a control. The results are shown in Table 11.

TABLE 11

| | Control Reference Example | scorch time |
|---|---|---|
| Example 72 | Reference Example 29 | 97 |
| Example 74 | Reference Example 31 | 98 |
| Example 76 | Reference Example 33 | 99 |

(2) Viscoelastic Property

The viscoelastic property was measured using Viscoelasticity Analyzer manufactured by Ueshima Seisakusho Co., Ltd.

Condition; temperature: −5° C. to 80° C. (temperature rising rate: 2° C./min), initial strain: 10%, dynamic strain: 2.5%, frequency: 10 Hz The decreasing rate (%) in the viscoelastic property (tan δ at 60° C.) of the vulcanized rubber obtained in Example 73, 75 and 77 with respect to the vulcanized rubber obtained in Reference Example 30, 32 and 34 was measured, using the vulcanized rubber obtained in Reference Example 30, 32 and 34 as a control. The results are shown in Table 12.

TABLE 12

| | Control Reference Example | The decreasing rate (%) |
|---|---|---|
| Example 73 | Reference Example 30 | 19 |
| Example 75 | Reference Example 32 | 7 |
| Example 77 | Reference Example 34 | 14 |

Example 78

When a steel cord treated by brass plating is coated by the rubber composition obtained in the procedure 2 of Example 10, a belt is obtained. Using the resulting belt, a green time is molded according to a usual production method, and the resultant green tire is heated and pressed in a vulcanizer, to obtain a vulcanized tire.

Example 79

The rubber composition obtained in the procedure 2 of Example 10 is extrusion-processed, to obtain a member for tread. Using the resulting member for tread, a green tire is molded according to a usual production method, and the resultant green tire is heated and pressed in a vulcanizer, to obtain a vulcanized tire.

Example 80

The rubber composition obtained in the procedure 2 of Example 10 is extrusion-processed, to prepare a rubber composition having a shape corresponding to the shape of a carcass, and the rubber composition is pasted on the upper and lower sides of a carcass fiber cord made of polyester, to obtain a carcass. Using the resulting carcass, a green tire is molded according to a usual production method, and the resultant green tire is heated and pressed in a vulcanizer, to obtain a vulcanized tire.

Example 81

A rubber composition is obtained in the same manner as in Example 10 excepting that 0.2 parts by weight of N-(cyclohexylthio)-phthalimide (CTP) is further blended by kneading in the procedure 2 of Example 10.

Example 82

The rubber composition obtained in the procedure 2 of Example 81 was vulcanization-treated at 145° C., to obtain vulcanized rubber.

Example 83

Production of Rubber Composition

<Procedure 1>

Using a Banbury mixer (manufactured by Toyo Seiki Seisakusho Co., Ltd., 600 ml Laboplastomill), 80 parts by weight of natural rubber (RSS#1), 20 parts by weight of polybutadiene rubber (manufactured by JSR, trace name "BR01"), 40 parts by weight of FEF (manufactured by Asahi Carbon Co., Ltd., trade name "Asahi #60"), 40 parts by weight of heavy calcium carbonate, 3 parts by weight of stearic acid, 5 parts by weight of zinc oxide, 1 part by weight of an antioxidant (N-phenyl-N'-1,3-dimethylbutyl-p-phenylenediamine (6PPD): trade name "Antigen (registered trademark) 6C", manufactured by Sumitomo Chemical Co., Ltd.), 1 part by weight of an antioxidant Polymerized-2,2,4-trimethyl-1,2-dihydroquinoline (TMDQ) and 2 parts by weight of sodium (2Z)-4-[(4-aminophenyl)amino]-4-oxo-2-butenoate di-hydrate obtained in the above-described Example 3 were kneaded to obtain a kneaded material. In this step, various chemicals and fillers were charged, then, kneaded at a mixer set temperature of 120° C. and a mixer rotating speed 50 rpm for 5 minutes. The temperature of the kneaded material when kneading was completed was 171° C.

<Procedure 2>

In an open roll mill, the rubber composition obtained from the procedure 1n, 1 part by weight of a vulcanization accelerator N-cyclohexyl-2-benzothiazole sulfenamide (CBS) and 2 parts by weight of sulfur were blended by kneading at a temperature of 60 to 80° C., to obtain a rubber composition.

Example 84

Production of Vulcanized Rubber

The rubber composition obtained in the procedure 2 of Example 83 was vulcanization-treated at 145° C., to obtain vulcanized rubber.

Reference Example 35

A rubber composition was obtained in the same manner as in Example 83 excepting that sodium (2Z)-4-[(4-aminophenyl)amino]-4-oxo-2-butenoate di-hydrate was not used in Example 83.

Reference Example 36

The rubber composition obtained in the procedure 2 of Reference Example 35 was vulcanization-treated at 145° C., to obtain vulcanized rubber.

The dynamic viscoelastic property was measured and the dynamic magnification was calculated as described below.

(1) Dynamic Viscoelastic Property

The dynamic viscoelastic property was measured using a viscoelasticity measuring apparatus RSA-3 manufactured by TA INSTRUMENTS.

Condition; temperature: −40 to 80° C., dynamic strain: 0.1%, frequency: 1 to 10 Hz (2) Dynamic Magnification Base on the results obtained in (1), frequency dependency at a reference temperature of 22° C. (master curve) was determined, and the complex elastic modulus when the frequency is 1 Hz was defined as the static elastic modulus and the complex elastic modulus when the frequency is 100 Hz was defined as the dynamic elastic modulus, and calculation thereof was effected according to formula (1).

Dynamic magnification=dynamic elastic modulus (Pa)/static elastic modulus (Pa)   formula (1)

Based on the rubber composition obtained in Reference Example 36 as a control, the dynamic magnification of the rubber composition obtained in Example 84 decreased by 4%, thus, an improvement in the dynamic magnification was confirmed.

Example 85

Production of Rubber Composition

<Procedure 1>

Using a Banbury mixer (manufactured by Toyo Seiki Seisakusho Co., Ltd., 600 ml Laboplastomill), 100 parts by weight of styrene-butadiene copolymerized rubber SBR#1502 (manufactured by Sumitomo Chemical Co., Ltd.,), 45 parts by weight of ISAF-HM (manufactured by Asahi Carbon Co., Ltd., trade name "Asahi #80"), 2 parts by weight of stearic acid, 3 parts by weight of zinc oxide, 1 part by weight of (2Z)-4-[(4-aminophenyl)amino]-4-oxo-2-butenoic acid, 1 part by weight of an antioxidant (N-phenyl-N'-1,3-dimethylbutyl-p-phenylenediamine (6PPD): trade name "Antigen (registered trademark) 6C", manufactured by Sumitomo Chemical Co., Ltd.) and 2 parts by weight of wax (manufactured by Nippon Seiro Co., Ltd. "OZOACE-0355") were blended by kneading, to obtain a rubber composition. This step was performed by charging various components, then, kneading them at a mixer rotating speed of 50 rpm for 5 minutes, and the rubber temperature in this operation was 160 to 175° C.

<Procedure 2>

In an open roll mill, the rubber composition obtained by the procedure 1, 3 parts by weight of a vulcanization accelerator N-cyclohexyl-2-benzothiazolyl sulfenamide (CBS) and 2 parts by weight of sulfur were blended by kneading at a temperature of 60 to 80° C., to obtain a rubber composition.

Example 86

Production of Vulcanized Rubber

The rubber composition obtained by the procedure 2 of Example 85 was thermally treated at 145° C., to obtain vulcanized rubber. This vulcanized rubber is suitable for a cap tread.

Example 87

Production of Rubber Composition

<Procedure 1>

Using a Banbury mixer (manufactured by Toyo Seiki Seisakusho Co., Ltd., 600 ml Laboplastomill), 100 parts by weight of a styrene-butadiene copolymerized rubber SBR#1502 (manufactured by Sumitomo Chemical Co., Ltd.), 35 parts by weight of ISAF-HM (manufactured by Asahi Carbon Co., Ltd., trade name "Asahi #80"), 2 parts by weight of stearic acid, 3 parts by weight of zinc oxide, 1 parts by weight of (2Z)-4-[(4-aminophenyl)amino]-4-oxo-2-butenoic acid, 1 part by weight of an antioxidant (N-phenyl-N'-1,3-dimethylbutyl-p-phenylenediamine (6PPD): trade name "Antigen (registered trademark) 6C", manufactured by Sumitomo Chemical Co., Ltd.) and 2 parts by weight of wax (manufactured by Nippon Seiro Co., Ltd. "OZOACE-0355") were blended by kneading, to obtain a rubber composition. This step was performed by charging various components, then, kneading them at a mixer rotating speed of 50 rpm for 5 minutes, and the rubber temperature in this operation was 160 to 175° C.

<Procedure 2>

In an open roll mill, the rubber composition obtained by the procedure 1, 2 parts by weight of a vulcanization accelerator N-cyclohexyl-2-benzothiazolyl sulfenamide (CBS), 0.5 parts by weight of a vulcanization accelerator diphenylguanidine (DPG), 0.8 parts by weight of a vulcanization accelerator dibenzothiazyl disulfide (MBTS) and 1 part by weight of sulfur were blended by kneading at a temperature of 60 to 80° C., to obtain a rubber composition.

Example 88

Production of Vulcanized Rubber for Under Tread

The rubber composition obtained by the procedure 2 in Example 87 was thermally treated at 145° C., to obtain vulcanized rubber. This vulcanized rubber is suitable for an under tread.

Example 89

Production of Rubber Composition

<Procedure 1>

Using a Banbury mixer (manufactured by Toyo Seiki Seisakusho Co., Ltd., 600 ml Laboplastomnill), 100 parts by weight of natural rubber (RSS#1), 45 parts by weight of HAF (manufactured by Asahi Carbon Co., Ltd., trade name "Asahi #70"), 3 parts by weight of stearic acid, 5 parts by weight of zinc oxide, 1 part by weight of (2Z)-4-[(4-aminophenyl)amino]-4-oxo-2-butenoic acid, 10 parts by weight of hydrous silica (manufactured by Tosoh Silica Corporation "Nipsil (registered trademark) AQ"), 2 parts by weight of an antioxidant FR (manufactured by Matsubara Sangyo, "Antioxidant FR"), 2 parts by weight of resorcin and 2 parts by weight of cobalt naphthenate were blended by kneading, to obtain a rubber composition. This step was performed by charging various components, then, kneading them at a mixer rotating speed of 50 rpm for 5 minutes, and the rubber temperature in this operation was 160 to 175° C.

<Procedure 2>

In an open roll mill, the rubber composition obtained by the procedure 1, 1 part by weight of a vulcanization accelerator N,N-dicyclohexyl-2-benzothiazolyl sulfenamide (DCBS), 6 parts by weight of sulfur and 3 parts by weight of a methoxylated methylol melamine resin (manufactured by Sumitomo Chemical Co., Ltd., "Sumikanol 507AP") were blended by kneading at a temperature of 60 to 80° C., to obtain a rubber composition.

Example 90

Production of Vulcanized Rubber

The rubber composition obtained by the procedure 2 of Example 89 was thermally treated at 145° C., to obtain vulcanized rubber. This vulcanized rubber is suitable for a belt.

Example 91

Production of Rubber Composition

<Procedure 1>
Using a Banbury mixer (manufactured by Toyo Seiki Seisakusho Co., Ltd., 600 ml Laboplastomill), 100 parts by weight of halogenated butyl rubber (manufactured by Exxon Mobile Corporation, "Br-IIR2255"), 60 parts by weight of GPF, 1 part by weight of stearic acid, 3 parts by weight of zinc oxide, 1 part by weight of (2Z)-4-[(4-aminophenyl)amino]-4-oxo-2-butenoic acid and 10 parts by weight of a paraffin oil (manufactured by Idemitsu Kosan Co., Ltd., "Diana Process Oil") were blended by kneading, to obtain a rubber composition. This step was performed by charging various components, then, kneading them at a mixer rotating speed of 50 rpm for 5 minutes, and the rubber temperature in this operation was 160 to 175° C.

<Procedure 2>
In an open roll mill, the rubber composition obtained by the procedure 1, 1 part by weight of an antioxidant (condensate of aniline and acetone (TMDQ)), 1 part by weight of a vulcanization accelerator dibenzothiazyl disulfide (MBTS) and 2 parts by weight of sulfur were blended by kneading at a temperature of 60 to 80° C., to obtain a rubber composition.

Example 92

Production of Vulcanized Rubber

The rubber composition obtained by the procedure 2 of Example 91 was thermally treated at 145° C., to obtain vulcanized rubber. This vulcanized rubber is suitable for an inner liner.

Example 93

Production of Rubber Composition

<Procedure 1>
Using a Banbury mixer (manufactured by Toyo Seiki Seisakusho Co., Ltd., 600 ml Laboplastomill), 40 parts by weight of natural rubber (RSS#3), 60 parts of polybutadiene rubber (manufactured by Ube Industries Ltd., "BR150B"), 50 parts by weight of FEF, 2.5 parts by weight of stearic acid, 3 parts by weight of zinc oxide, 1 part by weight of (2Z)-4-[(4-aminophenyl)amino]-4-oxo-2-butenoic acid, 2 parts by weight of an antioxidant (N-phenyl-N'-1,3-dimethylbutyl-p-phenylenediamine (6PPD): trade name "Antigen (registered trademark) 6C", manufactured by Sumitomo Chemical Co., Ltd.), 10 parts by weight of an aromatic oil (manufactured by COSMO OIL Co., Ltd., "NC-140") and 2 parts by weight of wax (manufactured by Ouchi Shinko Chemical Industrial Co., Ltd., "Sannoc (registered trademark) wax") were blended by kneading, to obtain a rubber composition. This step was performed by charging various components, then, kneading them at a mixer rotating speed of 50 rpm for 5 minutes, and the rubber temperature in this operation was 160 to 175° C.

<Procedure 2>
In an open roll mill, the rubber composition obtained by the procedure 1, 0.75 parts by weight of a vulcanization accelerator N-tert-butyl-2-benzothiazolyl sulfonamide (BBS) and 1.5 parts by weight of sulfur were blended by kneading at a temperature of 60 to 80° C., to obtain a rubber composition.

Example 94

Production of Vulcanized Rubber

The rubber composition obtained by the procedure 2 of Example 93 was thermally treated at 145° C., to obtain vulcanized rubber. This vulcanized rubber is suitable for a side wall.

Example 95

Production of Rubber Composition

<Procedure 1>
Using a Banbury mixer (manufactured by Toyo Seiki Seisakusho Co., Ltd., 600 ml Laboplastomill), 70 parts by weight of natural rubber (TSR20), 30 parts by weight of styrene-butadiene copolymerized rubber SBR#1502 (manufactured by Sumitomo Chemical Co., Ltd.), 60 parts by weight of N339 (manufactured by Mitsubishi Chemical Corporation), 2 parts by weight of stearic acid, 5 parts by weight of zinc oxide, 7 parts by weight of a process oil (manufactured by Idemitsu Kosan Co., Ltd., "Diana Process PS32") and 1 part by weight of (2Z)-4-[(4-aminophenyl)amino]-4-oxo-2-butenoic acid were blended by kneading, to obtain a rubber composition. This step was performed by charging various components, then, kneading them at a mixer rotating speed of 50 rpm for 5 minutes, and the rubber temperature in this operation was 160 to 175° C.

<Procedure 2>
In an open roll mill, the rubber composition obtained by the procedure 1, 1 part by weight of a vulcanization accelerator N-tert-butyl-2-benzothiazolyl sulfonamide (BBS), 3 parts by weight of sulfur, 1 part by weight of an antioxidant (N-phenyl-N'-1,3-dimethylbutyl-p-phenylenediamine (6PPD): trade name "Antigen (registered trademark) 6C", manufactured by Sumitomo Chemical Co., Ltd.) and 1 part by weight of an antioxidant (condensate of aniline and acetone (TMDQ)) were blended by kneading at a temperature of 60 to 80° C., to obtain a rubber composition.

Example 96

Production of Vulcanized Rubber

The rubber composition obtained by the procedure 2 of Example 95 was thermally treated at 145° C., to obtain vulcanized rubber. This vulcanized rubber is suitable for a carcass.

Example 97

Production of Rubber Composition

<Procedure 1>
Using a Banbury mixer (manufactured by Toyo Seiki Seisakusho Co., Ltd., 600 ml Laboplastomill), 100 parts by weight of styrene-butadiene copolymerized rubber SBR#1500 (manufactured by JSR), 78.4 parts by weight of silica (trade name "Ultrasil (registered trademark) VN3-G", manufactured by Degussa), 6.4 parts by weight of carbon black (trade name "N-339", manufactured by Mitsubishi Chemical Corporation), 6.4 parts by weight of a silane coupling agent (bis(3-triethoxysilylpropyl)tetrasulfide: trade name "Si-69", manufactured by Degussa), 47.6 parts by weight a process oil (trade name "NC-140", manufactured by COSMO OIL Co., Ltd.), 1.5 parts by weight of an antioxidant (N-phenyl-N'-1,3-dimethylbutyl-p-phenylenediamine (6PPD): trade name "Antigen (registered trademark) 6C", manufactured by Sumitomo Chemical Co., Ltd.), 2 parts by weight of zinc oxide, 2 parts by weight of stearic acid and 3 parts by weight of (2Z)-4-[(4-aminophenyl)amino]-4-oxo-2-butenoic acid were blended by kneading, to obtain a rubber composition. This step is operated in the temperature range of 70° C. to 120° C., and various components are charged, then, kneaded at a mixer rotating speed of 80 rpm for 5 minutes, subsequently, kneaded at a mixer rotating speed of 100 rpm for 5 minutes.

<Procedure 2>

In an open roll mill, the rubber composition obtained by the procedure 1, 1 part by weight of a vulcanization accelerator N-cyclohexyl-2-benzothiazolyl sulfenamide (CBS), 1 part by weight of a vulcanization accelerator diphenylguanidine (DPG), 1.5 parts by weight of wax (trade name "Sannoc (registered trademark) N", manufactured by Ouchi Shinko Chemical Industrial Co., Ltd.) and 1.4 parts by weight of sulfur were blended by kneading at a temperature of 30 to 80° C., to obtain a rubber composition.

Example 98

Production of Vulcanized Rubber

The rubber composition obtained by the procedure 2 of Example 97 was thermally treated at 160° C., to obtain vulcanized rubber. This vulcanized rubber is suitable for a cap tread.

Example 99

Production of Rubber Composition

A rubber composition is obtained in the same manner as in Example 95 excepting that solution polymerized SBR ("Asaprene (registered trademark)" manufactured by Asahi Kasei Chemicals Corporation) is used instead of the styrene-butadiene copolymerized rubber SBR#1500 (manufactured by JSR) in Example 97.

Example 100

Production of Vulcanized Rubber

The rubber composition obtained by the procedure 2 of Example 99 was thermally treated at 160° C., to obtain vulcanized rubber. This vulcanized rubber is suitable for a cap tread.

Example 101

Production of Rubber Composition

A rubber composition is obtained in the same manner as in Example 95 excepting that SBR#1712 (manufactured by JSR) is used instead of the styrene-butadiene copolymerized rubber SBR#1500 (manufactured by JSR), the use amount of the process oil is changed to 21 parts by weight and the timing of charging zinc oxide is changed to the procedure 2, in Example 97.

Example 102

Production of Vulcanized Rubber

The rubber composition obtained by the procedure 2 of Example 101 is thermally treated at 160° C., to obtain vulcanized rubber. This vulcanized rubber is suitable for a cap tread.

Example 103

Production of Rubber Composition

<Procedure 1>

Using a Banbury mixer (manufactured by Toyo Seiki Seisakusho Co., Ltd., 600 ml Laboplastomill), 80 parts by weight of natural rubber (RSS#1), 20 parts by weight of polybutadiene rubber (manufactured by JSR, trade name "BR01"), 40 parts by weight of FEF (manufactured by Asahi Carbon Co., Ltd., trade name "Asahi #60"), 40 parts by weight of heavy calcium carbonate, 3 parts by weight of stearic acid, 5 parts by weight of zinc oxide, 1 part by weight of an antioxidant (N-phenyl-N'-1,3-dimethylbutyl-p-phenylenediamine (6PPD): trade name "Antigen (registered trademark) 6C", manufactured by Sumitomo Chemical Co., Ltd.), 1 part by weight of an antioxidant Polymerized-2,2,4-trimethyl-1,2-dihydroquinoline (TMDQ) and 2 parts by weight of (2Z)-4-[(4-aminophenyl)amino]-4-oxo-2-butenoic acid are blended by kneading, to obtain a rubber composition. This step is performed by charging various components, then, kneading them at a mixer rotating speed of 50 rpm for 5 minutes, and the rubber temperature in this operation is 160 to 175° C.

<Procedure 2>

In an open roll mill, the rubber composition obtained by the procedure 1, 1 part by weight of a vulcanization accelerator N-cyclohexyl-2-benzothiazole sulfenamide (CBS) and 2 parts by weight of sulfur are blended by kneading at a temperature of 60 to 80° C., to obtain a rubber composition.

Example 104

Production of Vulcanized Rubber

The rubber composition obtained by the procedure 2 of Example 103 is thermally treated at 145° C., to obtain vulcanized rubber. This vulcanized rubber is suitable as vibration-proof rubber.

Example 105

Production of Rubber Composition

<Procedure 1>

Using a Banbury mixer (manufactured by Toyo Seiki Seisakusho Co., Ltd., 600 ml Laboplastomill), 50 parts by weight of natural rubber (RSS#1), 50 parts by weight of styrene-butadiene copolymerized rubber SBR#1500 (manufactured by JSR), 50 parts by weight of HAF (manufactured by Asahi Carbon Co., Ltd., trade name "Asahi #70"), 2 parts by weight of stearic acid, 3 parts by weight of zinc oxide, 2 parts by weight of an antioxidant Polymerized-2,2,4-trimethyl-1,2-dihydroquinoline (TMDQ) and 2 parts by weight of (2Z)-4-[(4-aminophenyl)amino]-4-oxo-2-butenoic acid are blended by kneading, to obtain a rubber composition. This step is performed by charging various components, then, kneading them at a mixer rotating speed of 50 rpm for 5 minutes, and the rubber temperature in this operation is 1.60 to 175° C.

<Procedure 2>

In an open roll mill, the rubber composition obtained by the procedure 1, 1.5 parts by weight of a vulcanization accelerator N-t-butyl-2-benzothiazole sulfonamide (NS) and 2 parts by weight of sulfur are blended by kneading at a temperature of 60 to 80° C., to obtain a rubber composition.

Example 106

Production of Vulcanized Rubber

The rubber composition obtained by the procedure 2 of Example 105 is thermally treated at 145° C., to obtain vulcanized rubber. This vulcanized rubber is suitable for a rubber belt.

Industrial Applicability

According to the rubber composition of the present invention, the viscoelastic property of vulcanized rubber obtained from this rubber composition can be improved.

The invention claimed is:

1. A salt represented by formula (III):

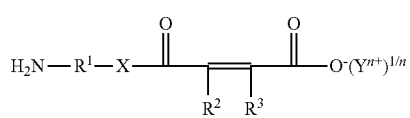

in formula (III), $R^1$ represents an optionally substituted alkanediyl group having 2 to 12 carbon atoms, an optionally substituted cycloalkanediyl group having 3 to 12 carbon atoms or a *—$B^1$—Ar—$B^2$—* group, * represents a connecting bond, $B^1$ represents a single bond or an alkanediyl group having 1 to 12 carbon atoms, $B^2$ represents a single bond or an alkanediyl group having 1 to 12 carbon atoms, Ar represents an optionally substituted di-valent aromatic hydrocarbon group having 6 to 12 carbon atoms, $R^2$ and $R^3$ represent each independently a hydrogen atom, a halogen atom, an alkyl group having 1 to 6 carbon atoms, an aryl group having 6 to 12 carbon atoms, a hydroxy group or an alkoxy group having 1 to 6 carbon atoms, alternatively, are mutually linked to form an alkanediyl group having 2 to 12 carbon atoms, $Y^{n+}$ represents an n-valent metal cation, $NH_4^+$ or an n-valent organic cation, n represents 1 or 2, and X represents —NH— or —O—.

2. A hydrate of the salt represented by formula (III) according to claim 1.

* * * * *